United States Patent [19]

Bruynes et al.

[11] 4,400,509
[45] Aug. 23, 1983

[54] SILYLATION PROCESS

[75] Inventors: Cornelis A. Bruynes, Koudekerk a/d Rijn; Theodorus K. Jurriens, Delft, both of Netherlands

[73] Assignee: Gist-Brocades N.V., Delft, Netherlands

[21] Appl. No.: 280,350

[22] Filed: Jul. 6, 1981

[30] Foreign Application Priority Data

Jul. 4, 1980 [NL] Netherlands .................. 8003891
Sep. 5, 1980 [NL] Netherlands .................. 8005041

[51] Int. Cl.³ .................................. C07D 501/04
[52] U.S. Cl. .................. 544/315; 260/245.2 R; 260/239.1; 544/26; 544/27; 548/136; 548/251; 548/255; 548/263; 548/337
[58] Field of Search ............. 544/26, 242, 26, 27, 544/315; 260/245.2 R; 548/136, 251, 255, 263, 337

[56] References Cited

PUBLICATIONS

Harpp et al., JACS vol. 100, p. 1222 (1978).
Evans, JACS vol. 99, 5009 (1977).
Cephalosporins and Pencillins pp. 179-180 (1972) edited by E. Flynn (Academic Press, N.Y.).

*Primary Examiner*—Nicholas S. Rizzo
*Attorney, Agent, or Firm*—Hammond & Littell, Weissenberger and Muserlian

[57] ABSTRACT

An improved process for the trimethylsilylation of organic compounds with at least one active hydrogen atom with hexamethyldisilazane, the improvement comprising effecting the reaction in the presence of 0.001 to 10 mole percent of a catalyst of the formula

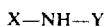

wherein X and Y are individually an electron-withdrawing group or when X is an electron-withdrawing group, Y is selected from the group consisting of hydrogen and trialkylsilyl of 1 to 6 carbon atoms or X and Y together with the nitrogen atom to which they are attached form a cyclic electron-withdrawing group and novel trimethylsilylated thiols of the formula

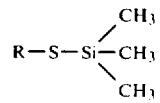

wherein R is a 5-or 6-membered heterocycle having at least one nitrogen or sulfur heteroatom and optionally substituted with at least one member of the group consisting of alkyl of 1 to 6 carbon atoms, phenyl, trimethylsilyl, trimethylsilyloxycarbonylmethyl and alkylamino of 1 to 6 carbon atoms, and novel trimethylsilylated 3'-substituted cephalosporanic acid derivatives.

10 Claims, No Drawings

SILYLATION PROCESS

STATE OF THE ART

In preparative organic chemistry, there is a growing interest in the use of the trimethylsilyl group for the protection of reactive groups as well as for the modification of physical properties such as volatility and solubility [see for example Cooper, Chem. and Ind. 1978, p. 794].

Silylating agents used on a large scale are, for example, trimethylchlorosilane and dimethyldichlorosilane. Due to the fact that silylation reactions are equilibrium reactions, it is essential to remove the hydrogen chloride which is generated in the reaction as soon as possible to shift the equilibrium to the side of the desired products and this can be done by the addition of a suitable tertiary amine to the reaction mixture. The amine reacts with the hydrogen chloride with the formation of the corresponding ammonium salt which is usually poorly soluble in the reaction mixture and the removal of the said ammonium salt is usually necessary before the product can be purified which requires the use of large amounts of a suitable solvent. However, it is often unavoidable that traces of ammonium salt remain in the product.

Other silylating agents which are frequently used, e.g. N,O-(bis-trimethylsilyl)-acetamide, N,N'-bis-(trimethylsilyl)-urea, N-trimethylsilyl-N,N'-diphenylurea, N-trimethylsilylimidazole and trimethylsilyldiethylamine which compounds often are prepared from trimethylchlorosilane have the disadvantage that the silylated product has to be separated from the remainder which is left from the silylating agent. Another silylating agent which is used on a large scale is 1,1,1-trimethyl-N-(trimethylsilyl)-silanamine which is known under its common name hexamethyldisilazane or HMDS, which has the advantage that the only by-product is gaseous ammonia which is therefore easily removed. Furthermore, HMDS is a relatively cheap reagent which makes it attractive for industrial processes.

However, an important disadvantage of HMDS is that it reacts slowly in many instances, and in some cases it does not react al all [see e.g. Langer, J. Org. Chem. Vol. 23, p. 50 (1958)]. Consequently, high reaction temperatures and/or long reaction times are necessary to complete the silylation which makes the method less attractive and unsuitable for heat-sensitive compounds. Furthermore, a large excess of HMDS is often required.

Therefore, much attention has been paid to the catalysis of silylation reactions with HMDS to lower the reaction temperature and/or to shorten the reaction time. Examples of catalysts are amine salts (see e.g. DOS No. 2,507,882), trimethylchlorosilane [see Langer, J. Org. Chem. Vol. 23, p. 50 (1958)], inorganic acids such a sulfuric acid [see Armitage, Inorg. Synth., Vol. 15, p. 207 (1974)], hydrogen chloride, phosphoric acid and their ammonium salts (see e.g. NL No. 76-13342), Lewis acids such as boron trifluoride and aluminum trichloride (see also NL No. 76-13342), bis-(trialkylsilyl)-sulfate (see e.g. GE No. 26-49536), (fluoralkyl)sulfonic acids (see e.g. GE No. 27-57936) and imidazole [see Harpp, J. Amer. Chem. Soc., Vol. 100 p. 1222 (1978)]. However, even with these catalysts, high reaction temperatures, an excess of HMDS and sometimes very long reaction times, i.e. up to 48 hours, are still necessary to obtain a sufficient conversion to the desired silyl derivative.

OBJECTS OF THE INVENTION

It is an object of the invention to provide an improved process for silylation of organic compounds with at least one active hydrogen atom with hexamethyldisilazane in the presence of nitrogen containing catalysts.

It is another object of the invention to provide novel trimethylsilylated thiols.

It is another object of the invention to provide novel trimethylsilylated 3'-substituted cephalosporanic acid derivatives.

These and other objects and advantages of the invention will become obvious from the following detailed description.

THE INVENTION

In the improved process of the invention for the trimethylsilylation of organic compounds with at least one active hydrogen atom with hexamethyldisilazane, the improvement comprises effecting the reaction in the presence of 0.001 to 10 mole percent of a catalyst of the formula $$X-NH-Y \qquad 1$$

wherein X and Y are individually an electron-withdrawing group or when X is an electron-withdrawing group, Y is selected from the group consisting of hydrogen and trialkylsilyl of 1 to 6 carbon atoms or X and Y together with the nitrogen atom to which they are attached form a cyclic electron-withdrawing group.

Suitable electron-withdrawing groups in catalysts of the above formula are acyl groups, sulfonyl groups and phosphoryl groups. For more details about electron-withdrawing groups see for instance: Hammet, Physical Organic Chemistry, McGraw-Hill Book Company, New York, 1970, p. 347 ff, and Roberts et al Modern Organic Chemistry, W. A. Benjamin Inc., New York, 1967, p. 553 ff.

Examples of suitable electron-withdrawing groups are those of the formulae:

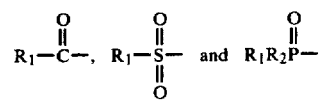

wherein $R_1$ and $R_2$ are individually selected from the group consisting of alkyl optionally substituted by at least one halogen, aryl optionally substituted by at least one member of the group consisting of halogen, alkyl, alkoxy and nitro, alkoxy, aryloxy optionally substituted with at least one member of the group consisting of halogen, alkyl and nitro or $R_3R_4N-$ wherein $R_3$ and $R_4$ are individually selected from the group consisting of hydrogen, trialkylsilyl and alkyl.

Examples of suitable electron-withdrawing groups which form a cyclic system together with the nitrogen atom are those of the formula $-A-Z-B-$ wherein A is

B is selected from the group consisting of

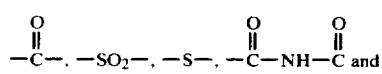

and Z is selected from the group consisting of alkylene, alkenylene and arylene optionally substituted by at least one halogen or alkyl.

Examples of more particularly suitable electron-withdrawing groups are those of the formulae:

 /I/ wherein $R_5$ is selected from the group consisting of alkyl optionally substituted by at least one halogen and aryl optionally substituted by at least one alkoxy or nitro,

 /II/ wherein $R_6$ is selected from the group consisting of methyl and aryl optionally substituted by at least one halogen or methyl, or $R_6$ is $R_7R_8N-$ wherein $R_7$ and $R_8$ are individually selected from the group consisting of hydrogen, trialkylsilyl and alkyl,

 /III/ wherein $R_9$ and $R_{10}$ are individually selected from the group consisting of alkoxy and aryloxy optionally substituted by halogen or nitro.

Examples of particularly suitable electron-withdrawing groups which form a cyclic system together with the nitrogen atom have the formulae:

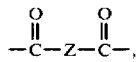 /I/ wherein Z is selected from the group consisting of alkenylene optionally substituted by at least one halogen or alkyl, and arylene optionally substituted by at least one halogen,

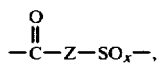 /II/ wherein x is 0 or 2, and Z is selected from the group consisting of alkylene and arylene.

Particularly preferred are those catalysts of the above formula wherein the electron-withdrawing groups have the formulae:

 /I/ wherein $R_5$ is selected from the group consisting of dihalomethyl, trihalomethyl, phenyl and naphthyl optionally substituted with methoxy,

 /II/ wherein $R_6$ is selected from the group consisting of methyl, phenyl optionally substituted by methyl or chlorine, amino, dialkylamino and trialkylsilylamino,

 /III/ wherein $R_9$ and $R_{10}$ are individually selected from the group consisting of methoxy, ethoxy, propoxy and phenyl optionally substituted by nitro or chlorine.

Similarly, examples of particularly preferred electron-withdrawing groups which form a cyclic system together with the nitrogen atom have the formulae:

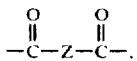 /I/ wherein Z is selected from the group consisting of ethylene, phenylene and naphthylene, each of which is optionally perhalo substituted, and

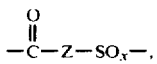 /II/ wherein x is 0 or 2, and Z is phenylene.

In this description, the alkyl, alkylene, alkenylene and alkoxy groups contain from one to six carbon atoms.

Examples of classes of compounds according to the above-mentioned definition possessing the desired catalytic properties are amides, sulfonamides, cyclic or open imides, cyclic or open sulfonimides, sulfamides, disulfonamides, acylphosphoramidates, sulfonylphosphoramidates and imidodiphosphates.

Suitable catalysts are for example trichloroacetamide, trifluoroacetamide, phthalimide, 3,4,5,6-tetrachlorophthalimide, 3,4,5,6-tetrabromophthalimide, 1,8-naphthalimide, maleimide, barbituric acid, saccharine, N-benzoyl-4-toluenesulfonamide, N-(2-methoxybenzoyl)-4-toluenesulfonamide, N-(1-naphthoyl)-4-toluenesulfonamide, N-benzoylbenzenesulfonamide, N-(2-methoxy-1-naphthoyl)-4-toluenesulfonamide, N-(2-methoxy-1-naphthoyl)-methanesulfonamide, di-(4-toluenesulfonyl)-amine, dimethyl N-(trichloroacetyl)-phosphoramidates, di-4-nitrophenyl N-(trichloroacetyl)-phosphoramidate, di-4-nitrophenyl N-(p-toluenesulfonyl)-phosphoramidate, diisopropyl N-(dichloroacetyl)-phosphoramidate, di-o-chlorophenyl N-(4-chlorophenylsulfonyl)-phosphoramidate, tetraphenyl imidodiphosphate, sulfamide, N,N-dimethylsulfamide, N,N'-bis-(trimethylsilyl)sulfamide, 1,2-benzisothiazol-3-(2H)-one and 4-benzoyloxy-1,2-dihydro-1-oxo-phthalazine. Particularly preferred catalysts are saccharine, di-4-nitrophenyl-N-(trichloroacetyl)phosphoramidate, di-4-nitrophenyl-N-(4-toluenesulfonyl)-phosphoramidate and tetraphenyl-imidodiphosphate.

The reaction may be carried out with or without an organic solvent at temperatures in the temperature range of 0° C. to 150° C. The solvent, if any, must be inert to the reactants as well as to the products and preferably will dissolve little or nothing of the ammonia generated in the reaction at the temperature at which the reaction is carried out, because due to equilibrium institution the rate of reaction will slow down at higher ammonia concentrations. Suitable solvents are straight, branched or cyclic hydrocarbons which may be substituted by one or more halogen atoms, for example, hexane, cyclohexane, dichloromethane and chloroform; aromatic hydrocarbons, for example benzene, toluene and xylene; alkyl esters of carboxylic acids, for example ethyl acetate and butyl acetate; nitriles, for example, acetonitrile and benzonitrile; dimethylformamide, dimethylsulfoxide, or mixtures thereof.

Organic compounds carrying one or more —OH, —NH—, —NH₂ or —SH groups can be silylated by the method of the present invention. Examples of such compounds are alcohols, amines, phenols, thiophenols, acids, amides, sulfonamides, thioamides, phosphoramides, amino acids, heterocyclic compounds, penicillanic and cephalosporanic acids derivatives, hydrazines, N-hydroxy-succinimides, hydroxylamines, thiols and enolisable ketones. Due to the large number of classes of organic compounds which have one or more —OH, —NH—, —NH₂ or —SH groups, the above enumeration is not to be considered to be limiting upon the general scope of the present invention.

By using the catalysts of the present invention, the original disadvantages of the use of HMDS as a silylating agent, i.e. long reaction times and/or high reaction temperatures and/or the use of a large excess of the silylating agent have been overcome. Now, the silylation reactions can be performed in a short time and/or at low reaction temperatures and a small excess of silylating agent is usually sufficient. Furthermore, under these reaction conditions, a cleaner reaction mixture is formed, through which a purer product and in many cases a higher yield is obtained. Another advantage of the improved method of the present invention is that it has now become possible to silylate compounds of which it is known that they do not react with HMDS, in a short time by using the catalysts of the invention. Examples of such compounds are tertiary alcohols [see Langer c.s. J. Org. Chem., Vol. 23, p 50 (1958)], phthalimide [see Harpp c.s., J. Amer. Chem. Soc., Vol. 100, p, 1222 (1978)] and thiols.

Furthermore, by using the process of the invention, the preparation of N,O-bis-(trimethylsilyl) derivatives of penicillanic and cephalosporanic acid derivatives can be carried out in a simple way and with quantitative yields. These derivatives can be prepared in another way only with difficulty. [see Bortesi c.s., J. Pharm. Sci., Vol. 66 p. 1767 )1977)].

Another advantage of the present process for the preparation of silylated compounds exists in the fact that, as far as these compounds in their turn are used as silylating agents, such as for instance N-trimethylsilylimidazole, N,N'-bis-(trimethylsilyl)-urea etc., these compounds are not contaminated with ammonium salts which salts may lead to undesired side-reactions when using these silylating agents.

An example which illustrates the present invention is the silylation of urea. Silylation of urea without a catalyst takes 36 hours at circa 125° C. as described NL-Ser. No. 76-13342. Using ammonium chloride as a catalyst, it still takes 6 hours at 118° C. (Example III of the forementioned patent). However, with the present invention using saccharine as a catalyst, it has been found that a reaction time of 20 minutes suffices for completion of the reaction. Another example is the reaction of phenylhydrazine with HMDS. Without a catalyst, a yield of 12% was obtained after 12 hours at 130° C. [Fessenden c.s. J. Org. Chem., Vol. 26, p. 4638 (1961)]. Using ammonium chloride as a catalyst, a yield of 89% was obtained using the same reaction conditions. Using saccharine as a catalyst, only 2.5 hours were required to obtain the same yield of silylated product.

Reactions of HMDS with tertiary alcohols, which were known not to react with HMDS, even not in the presence of trimethylchlorosilane as a catalyst [Langer c.s. J. Org. Chem., Vol. 23, p. 50 (1958)], now run fast to very fast under the influence of the above-described catalysts. For example, t-amyl alcohol reacts in three hours with HMDS to form the trimethylsilyl ether using saccharine as a catalyst, and 2-methyl-n-hexanol reacts in only 15 minutes to form the trimethylsilyl derivative in a yield of 92% using di-4-nitrophenyl N-(4-toluenesulfonyl)-phosphoramidate as a catalyst. The reaction of phthalimide with HMDS also shows the advantages of the use of the catalysts of the invention. Silylation of phthalimide with hexamethyldisilazane and imidazole as a catalyst requires a two days' reflux [Harpp c.s., J. Amer. Chem. Soc., Vol. 100, p. 1222 (1978)] and it has now been found that the saccharine catalyzed silylation of phthalimide with HMDS is completed within 1.5 hours and gives substantially higher yields.

Moreover, the improved process of the invention, for the silylation of HMDS provides the possibility to prepare trimethylsilyl derivatives of organic compounds which could not be silylated according to the methods described till now in the literature. This applies particularly to certain organic thiols.

According, another feature of the invention is the preparation of trimethylsilyl substituted compounds of the formula

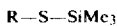

R—S—SiMe₃ wherein R is a five- or six membered heterocyclic having one or more nitrogen or sulfur atoms as the hetero atoms, which group may be substituted with at least one member of the group consisting of alkyl, phenyl, trimethylsilyl, alkylamino and trimethylsilyloxycarbonylmethyl.

Examples of the above-mentioned R are a 1,3,4-thiadiazolyl, a 1,2,3,4-tetrazolyl, a 1,2,3-triazolyl, a 1,2,4-triazolyl, an imidazolyl or a pyrimidyl optionally substituted with methyl, phenyl, methylamino, trimethylsilyl or trimethylsilyloxycarbonylmethyl. Compounds of the said formula are for example (5-methyl-1,3,4-thiadiazole-2-thio)-trimethylsilane, 1-methyl-5-trimethylsilylthiotetrazole, 1-trimethylsilyl-5-trimethylsilylthio-1,2,3-triazole, 1-methyl-2-(trimethylsilylthio)-imidazole, 1-trimethylsilyl-3-trimethylsilylthio-1H-1,2,4-triazole, 1-phenyl-5-trimethylsilylthio-1H-tetrazole, 4,6-dimethyl-2-(trimethylsilylthio)-pyrimidine, 2-methylamino-5-trimethylsilylthio-1,3,4-thiadiazole, trimethylsilyl 5-trimethylsilylthio-1H-tetrazolyl-1-acetate, trimethylsilyl 5-trimethylsilylthio-1,3,4-thiadiazolyl-2-acetate.

These trimethylsilylated thiols are useful intermediates in the preparation of valuable compounds by a new method. Examples of such valuable compounds are therapeutically active 3'-thiosubstituted cephalosporins or intermediates therefore and they are prepared by reacting the trimethylsilylated thiols with the corresponding 3'-halo substituted cephalosporins. This new method for the preparation of these cephalosporins is described in Dutch patent application Ser. No. 80.05041. Other uses of trimethylsilylthio compounds have been described for instance by Mukaiyama [Chem. Lett., p. 187, 1974 and Chem. Lett., p. 1013, 1974] and by Evans [J. Amer. Chem. Soc., Vol. 99, p. 5009 (1977)].

Accordingly, another feature of the invention are the new compounds of the formula

wherein R is a five or six-membered heterocyclic group having one or more nitrogen or sulfur atoms as the hetero atoms, which groups may be substituted by at least one member of the group consisting of alkyl, phenyl, trimethylsilyl, alkylamino and trimethylsilyloxycarbonylmethyl.

Examples of the above-mentioned group R are a 1,3,4-thiadiazolyl, a 1,2,3,4-tetrazolyl, a 1,2,3-triazolyl, a 1,2,4-triazolyl, an imidazolyl or a pyrimidyl optionally substituted by methyl, phenyl, methylamino, trimethylsilyl or trimethylsilyloxycarbonylmethyl. Compounds according to the above formula are for example (5-methyl-1,3,4-thiadiazole-2-thio)trimethylsilane, 1-methyl-5-trimethylsilylthiotetrazole, 1-trimethylsilyl-5-trimethylsilylthio-1,2,3-triazole, 1-methyl-2-(trimethylsilylthio)-imidazole, 1-trimethylsilyl-3-trimethylsilylthio-1H-1,2,4-triazole, 1-phenyl-5-trimethylsilylthio-1H-tetrazole, 4,6-dimethyl-2-(trimethylsilylthio)-pyrimidine, 2-methylamino-5-trimethylsilylthio-1,3,4-thiadiazole, trimethylsilyl-5-trimethylsilylthio-1H-tetrazolyl-1-acetate, trimethylsilyl 5-trimethylsilylthio-1,3,4-thiadiazolyl-2-acetate. These trimethylsilylated thiols are useful intermediates.

Still another feature of the invention are the new compounds trimethylsilyl 7-phenylacetamido-3-(1-methyl-1H-tetrazolyl-1-thio)-methyl-3-cephem-4-carboxylate-1-oxide, N,O-bis-(trimethylsilyl)-7-phenylacetamido-3-(1H-1,2,3-triazolyl-5-thio)-methyl-3-cephem-4-carboxylic acid-1-oxide, trimethylsilyl 7-trimethylsilylamino-3-(5-methyl-1,3,4-thiadiazolyl-2)thiomethyl-3-cephem-4-carboxylate, trimethylsilyl 7-trimethylsilylamino-3-(1-trimethylsilyl-1H-1,2,3-triazolyl-5)-thiomethyl-3-cephem-4-carboxylate, trimethylsilyl 7-trimethylsilylamino-3-(1-methyl-1H-tetrazolyl-5-)-thiomethyl-3-cephem-4-carboxylate, trimethylsilyl 7-phenylacetamido-3-(1-methyl-1H-tetrazolyl-5-thio)-methyl-3-cephem-4-carboxylate, trimethylsilyl 7-phenylacetamido-3-(1-trimethylsilyl-1H-1,2,3-triazolyl-5-thio)-methyl-3-cephem-4-carboxylate. These compounds are valuable compounds for the preparation of therapeutically active cephalosporines.

It will be clear to a person skilled in the art that the catalyst may be added to the reaction mixture as such, but also in a masked form, for instance as its silylated derivative, its sodium-salt or any other derivative which decomposes in the reaction mixture to the above mentioned catalytic compounds.

In the following examples there are described several preferred embodiments to illustrate the invention. However, it should be understood that the invention is not intended to be limited to the specific embodiments.

EXAMPLE 1

1-trimethylsilyloxydodecane

A. 90 mg of saccharin (0.5 mmole) were added to 18.6 g (0.1 mole) of 1-dodecanol and the mixture was heated to 130° C. 15.6 ml of hexamethyldisilazane (0.075 mole) were added over 8 minutes and the ammonia produced in the reaction was removed with a stream of dry nitrogen into water and tritated with 1 N HCl. It was found that the calculated amount of ammonia was evolved in 15 minutes after the beginning of the addition of hexamethyldisilazane and refluxing was continued for 10 minutes. Excess hexamethyldisilazane was distilled off at reduced pressure and the residue was vacuum distilled to yield 25.42 g (98.5%) of 1-trimethylsilyloxydodecane with a boiling point of at 120° C./0.5 mm Hg and $n_D 25 = 1.4268$.

B. 7.8 ml of hexamethyldisilazane (38 mmoles) were added to a refluxing solution of 9.3 g (50 mmoles) of 1-dodecanol and 51 mg (0.27 mmole) of saccharin in 50 ml of dichloromethane and by the method described in Example 1A, it was found that the calculated amount of ammonia was evolved after refluxing for one hour.

C. A solution of 9.30 g (50 mmoles) of 1-dodecanol and 70 mg (0.25 mmole) of dimethyl N-trichloroacetylphosphoramidate in 50 ml of dichloromethane was heated to reflux and 7.8 ml of hexamethyldisilazane (37.5 mmoles) were rapidly dropped in with a pressure equalized dropping funnel. It was found that the calculated amount of ammonia was evolved after refluxing for 75 minutes.

D. This preparation was carried out as described in Example 1C using 121 mg (0.25 mmole) of di-4-nitrophenyl-N-trichloroacetylphosphoramidate as the catalyst and the reaction was completed in 40 minutes.

E. Using 121 mg (0.25 mmole) of di-4-nitrophenyl-N-4-toluenesulfonylphosphoramidate as the catalyst, the reaction time was 60 minutes.

EXAMPLE 2

Trimethylsilyloxycyclohexane

By the method described in Example 1A, 15 g of cyclohexanol (0.15 mole) were silylated with 23.4 ml (0.112 mole) of hexamethyldisilazane added over 5 minutes and the silylation was catalyzed with 137 mg (0.75 mmole) of saccharin. The calculated amount of ammonia was evolved in 18 minutes and refluxing was then continued for 10 minutes. Excess hexamethyldisilazane was distilled off at reduced pressure and the residue was vacuum distilled to obtain 22.01 g (85.3%) of trimethylsilyloxyccclohexane with a boiling point of 53°–55° C. at 12 mm Hg and $n_D 25 = 1.4281$.

EXAMPLE 3

2-trimethylsilyloxy-2-methylbutane 21.9 ml of hexamethyldisilazane (0.105 mole) were added to a refluxing mixture of 17.6 g (0.20 mole) of 2-methyl-2-butanol (t-amylalcohol) and 0.18 g (1 mmole) of saccharin and the course of the silylation was followed as described in Example 1A. It was found that 50% of the calculated amount of ammonia was evolved in 18 minutes and refluxing was continued for 3.25 hours, after which time 98% of the calculated amount of ammonia was evolved. Distillation at normal pressure yielded 22.75 g (71%) of pure 2-trimethylsilyloxy-2-methylbutane with a boiling point of 129°-130° C. and a $n_D22=1.3980$. A forerun with a boiling point of 125°-129° C. (3.69 g) with $n_D22=1.3974$ contained 88% of 2-trimethylsilyloxy-2-methylbutane according to NMR analysis.

EXAMPLE 4

17$\beta$-trimethylsilyloxy-$\Delta^4$-androsten-3-one 246 mg of hexamethyldisilazane (1.5 mmole) were added to a refluxing suspension of 577 mg (2.0 mmoles) of 17$\beta$-hydroxy-$\Delta^4$-androsten-3-one and 1.8 mg (0.01 mmole) of saccharin in 10 ml of dichloromethane and the course of the reaction was followed by means of thin layer chromatography on Kieselgel 60 $F_{254}$ (Merck) with a 9+1 mixture of toluene and acetone as the eluents. It was found that after refluxing for 2 hours the starting material was no longer present and that one new product has been formed. By means of NMR spectroscopy, it was established that the product, obtained in quantitative yield after evaporation of the solvent in vacuo, was pure 17$\beta$-trimethylsilyloxy-$\Delta^4$-androsten-3-one with a melting point of 126°-128° C. (dec.).

EXAMPLE 5

1-trimethylsilyloxy-2-propene 24.28 g of allylalcohol (0.418 mole) and 0.36 g of saccharine (2 mmoles) were added to 50 ml of pentane and the mixture was heated to reflux 51 ml of hexamethyldisilazane (0.25 mole) were added to the mixture over 7 minutes and by titration of the ammonia generated during the reaction, it was found that the calculated amount was evolved in 1.5 hours. Distillation at normal pressure yielded 46.1 g (85%) of 1-trimethylsilyloxy-2-propene with a boiling point of 97°-100° C. and $n_D25=1.3943$.

EXAMPLE 6 penta(trimethylsilyl)-fructose 42 ml of hexamethyldisilazane (0.20 mole) were added dropwise in 8 minutes to a refluxing mixture of 7.20 g (40 mmoles) of fructose, 0.07 g (0.4 mmole) of saccharin, 24 ml of chloroform and 8 ml of pyridine and the ammonia evolved was absorbed in water and titrated with 1 N $H_2SO_4$. It was found that 0.10 mole of ammonia was evolved after refluxing for one hour and refluxing was continued for half an hour. The solvents were distilled off at normal pressure and the residue was vacuum distilled to yield 19.63 g (90.9%) of penta-(trimethylsilyl)-fructose with a boiling point of 138°-142° C. at 0.5 mm Hg and a $n_D25=1.4306$.

EXAMPLE 7

1-trimethylsilyloxyhexane

A. A mixture of 5.10 g (50 mmoles) 1-hexanol and 0.37 g (2.5 mmoles) of phthalimide was heated in an oil bath to 130° C. and 7.8 ml of hexamethyldisilazane (37.5 mmoles) were added. The evolution of ammonia was followed by absorbing it in water and titrating it with 1 N $H_2SO_4$ and it was found that the calculated amount of 25 mmoles of ammonia was evolved in 130 minutes.

B. The experiment was repeated with 2.5 mmoles of 3,4,5,6-tetrachlorophthalimide as the catalyst and the calculated amount of ammonia was evolved in 70 minutes.

C. The experiment was also repeated with 2.5 mmoles of 3,4,5,6-tetrabromophthalimide as the catalyst and it was found that the calculated amount of ammonia was evolved in 20 minutes.

D. A run without the addition of catalyst was also carried out and in that case, it was found that the calculated amount of ammonia was evolved after refluxing for 205 minutes.

E. 5.10 g (50 mmoles) of 1-hexanol were mixed with the catalysts mentioned in the following table, heated in an oil bath of 130° C. and 7.8 ml (37.5 mmoles) of hexamethyldisilazane were added. The time (t) in which half the theoretical amount of ammonia was evolved was measured. Further details are found in the following table.

TABLE 1

| catalyst | mol % of catalyst | t (minutes) |
|---|---|---|
| none | — | 22 |
| succinimide | 5.0 | 18 |
| 3,3-dimethylglutarimide | 5.0 | 16 |
| maleimide | 5.0 | 9 |
| 1,8-naphthalimide | 5.0 | 8 |
| 1,2-benzisothiazol-3(2H)-one | 5.0 | 9 |
| 4-benzoyloxy-1,2-dihydro-1-oxo-phthalazine | 5.0 | 7 |
| 3,4,5,6-tetrabromophthalimide | 2.0 | 4 |
| 3,4,5,6-tetrachlorophthalimide | 2.0 | 4 |
| barbituric acid | 2.0 | 12 |
| dimethyl N—trichloroacetyl-phosphoramidate | 0.1 | 7 |
| saccharin | 0.5 | 4 |
| di-4-nitrophenyl N—trichloro-acetylphosphoramidate | 0.1 | 1.5 |
| di-4-nitrophenyl N—4-toluene-sulphonylphosphoramidate | 0.1 | 1.5 |
| di-4-nitrophenyl N—trichloro-acetylphosphoramidate | 0.01 | 3 |
| di-4-nitrophenyl N—4-toluene-sulphonylphosphoramidate | 0.001 | 6 |
| tetraphenyl imidodiphosphate | 0.1 | 1 |
| tetraphenyl imidodiphosphate | 0.001 | 13 |

EXAMPLE 8

(2-methyl-2-hexoxy)-trimethylsilane

A mixture of 5.80 g (50 mmoles) of 2-methyl-2-hexanol and 25 mg (0.05 mmole) of di-4-nitrophenyl N-4-toluenesulfonylphosphoramidate was placed in an oil bath of 140° C. and 7.8 ml (37.5 mmoles) of hexamethyldisilazane were added. It was found that the calculated amount of ammonia was evolved after refluxing for 15 minutes. Vacuum distillation yielded 8.66 g (92%) of (2-methyl-2-hexoxy) trimethylsilane, with a boiling point of 54°-60° C. at 18 mm Hg and a $n_D25=1.4074$.

EXAMPLE 9

Reaction of hexamethyldisilazane with water 12.5 ml (60 mmoles) of hexamethyldisilazane were added dropwise over 5 minutes to a refluxing boiling solution of 740 mg (41 mmoles) of water and 21.4 mg (0.12 mmoles) of saccharin in 15 ml of dry acetonitrile. The ammonia evolved was led into water by means of a stream of nitrogen and titrated with 1 N sulfuric acid. After 4 minutes from the start of the dropwise addition, 50% of the calculated amount of ammonia had been collected and after 35 minutes, no more ammonia came free and the calculated amount had been collected.

EXAMPLE 10

N-trimethylsilyl-p-toluidine 25 ml of hexamethyldisilazane (0.12 mole) were added in 5 minutes to a mixture of 17.25 g (0.16 mole) of p-toluidine and 0.15 g (0.8 mmole) of saccharin which was heated to 130° C. in an oil bath. By titrating the ammonia evolved during the reaction, it was found that the calculated amount was evolved after refluxing for 2 hours and refluxing was continued for half an hour. The reaction mixture was vacuum distilled to yield 24.0 g (83%) of N-trimethylsilyl-p-toluidine with a boiling point of 98°–102° C. at 12–13 mm Hg.

EXAMPLE 11

Phenoxy-(trimethyl)-silane

To a refluxing solution of 19 g (0.2 mmole) of phenol and 80 mg (0.4 mmole) of saccharin in 15 ml of dichloromethane, 31 ml of hexamethyldisilazane (0.15 mmole) were added dropwise. After 25 minutes, the calculated amount of ammonia had been evolved as could be established by titration in the manner described herebefore and fractionation yielded 31.6 g (95%) of phenoxy-(trimethyl)-silane with a boiling point of 62°–63° C. at 12 mm Hg and $n_D25 = 1.4731$.

EXAMPLE 12 o-trimethylsilyloxytoluene 10.80 g (0.1 mole) of o-cresol were dissolved in 30 ml of dichloromethane and after 90 mg of saccharin (0.5 mmole) were added, the mixture was heated to reflux, 15.6 ml of hexamethyldisilazane (0.075 mole) were added and it was found that the theoretical amount of ammonia was evolved in 30 minutes. After evaporation of the solvent and the excess of hexamethyldisilazane, the residue was vacuum distilled to yield 16.91 g (93.9%) of o-trimethylsilyloxytoluene with a boiling point of 46°–53° C. at 0.5–0.7 mm Hg and $n_D25 = 1.4756$. A parallel run without saccharin needed 3.75 hours of refluxing to evolve the calculated amount of ammonia.

EXAMPLE 13

(2,6-di-sec-butylphenoxy)-trimethylsilane 7.8 ml of hexamethyldisilazane (37.5 mmoles) were added to a refluxing mixture of 10.4 g (50 mmoles) of 2,6-di-sec-butylphenol, 23 mg (0.05 mmole) of di-4-nitrophenyl N-trichloroacetylphosphoramidate and 20 ml of chloroform and the evolution of ammonia stopped after refluxing for 3½ hours. The chloroform was distilled off at reduced pressure and the residue was fractionated to yield 12.64 g (90%) of (2,6-di-sec-butylphenoxy)-trimethylsilane with a boiling point of 86°–90° C. at 0.4 mm Hg and $n_D25 = 1.4812$.

EXAMPLE 14

Trimethyl (phenylthio)-silane

A. 23.4 ml of hexamethyldisilazane (0.11 mole) were added over 10 minutes to a refluxing solution of 16.0 g (0.145 mole) of thiophenol and 135 mg (0.75 mmole) of saccharin in 25 ml of chloroform and by titration of the ammonia produced during the reaction, it was found that the silylation was completed after refluxing for 2.66 hours. The solvent and the excess of hexamethyldisilazane were distilled off at reduced pressure and the residue was fractionated to yield 24.4 (92.1%) of trimethyl-(phenylthio)-silane with a boiling point of 92°–95° C. at 12–13 mm Hg and $n_D25 = 1.5270$.

B. A mixture of 17.4 g (0.158 mole) of thiophenol, 135 mg (0.75 mmole) of saccharin and 24.7 ml (0.12 mole) of hexamethyldisilazane was refluxed for 2 hours and distillation yielded 23.9 g (83%) of trimethyl-(phenylthio)-silane with a boiling point of 88°–90° C. at 12 mm Hg and $n_D25 = 1.5308$.

EXAMPLE 15

(5-methyl-1,3,4-thiadiazolyl-2-thio)-trimethylsilane 15.6 ml of hexamethyldisilazane (0.075 mole) were added to a refluxing solution of 13.2 g (0.1 mole) of 2-mercapto-5-methyl-1,3,4-thiadiazole and 92 mg (0.5 mmole) of saccharin in 25 ml of toluene and by titrating the ammonia evolved, it was found that the reaction was completed after refluxing for 30 minutes. The toluene was distilled off at normal pressure and the residue was vacuum distilled to obtain 18.63 g (91.3%) of (5-methyl-1,3,4-thiadiazole-2-thio)-trimethylsilane with a boiling point of 150°–152° C. at 15 mm Hg. The distillate turned into a solid with a melting point of 67°–69° C. NMR (60 MHz; in $CCl_4$ with tetramethylsilane ($\Delta = 0$) as internal standard): two singlets at 0.56 and 2.42, integration ratio 3:1.

EXAMPLE 16

1-methyl-5-trimethylsilylthiotetrazole 0.582 g (5.0 mmoles) of 5-mercapto-1-methyltetrazole and 5.0 mg (0.03 mmole) of saccharin were dissolved in a mixture of 12 ml of ethyl acetate and 25 ml of dichloromethane and the mixture was refluxed while 1.26 ml of hexamethyldisilazane (5.5 mmoles) were added. The evolution of ammonia stopped after refluxing for one hour and volatile material was evaporated in vacuo to yield 0.94 g of 1-methyl-5-trimethylsilylthiotetrazole. NMR Spectrum ($CCl_4$): 2 singlets at 0.61 and 3.79 ppm, integration ratio 3:1.

EXAMPLE 17

1-trimethylsilyl-5-trimethylsilylthio-1,2,3-triazole 1.52 ml of hexamethyldisilazane (7.3 mmoles) were added to a refluxing mixture of 0.49 (4.86 mmoles) of 5-mercapto-1,2,3-(1H)-triazole, 5 mg (0.207 mmole) of saccharin, 10 ml of ethyl acetate and 15 ml of dichloromethane and the ammonia evolved was titrated with 1 N $H_2SO_4$ by the method described in Example 1A. It was found that 2 equivalents (4.9 mmoles) were evolved after refluxing for 30 minutes. Volatile materials were evaporated in vacuo to obtain 1.19 g (96%) of 1-trimethylsilyl-5-trimethylsilylthio-1,2,3-triazole NMR Spectrum was taken in carbon tetrachloride solution: $\Delta 0.31$ (9H); 0.48 (9H); 7.46 (1H).

EXAMPLE 18

1-methyl-2-(trimethylsilylthio)-imidazole

To a refluxing mixture of 1.14 g (10 mmoles) of 1-methyl-2-mercaptoimidazole, 18 mg (0.1 mmole) of saccharin and 20 ml of toluene under a stream of nitrogen, 1.5 ml of hexamethyldisilazane (7.2 mmoles) were added and the ammonia evolved was led into water by the nitrogen stream. By titration with 1 N sulfuric acid, it was established that the calculated amount of ammonia had been evolved within 40 minutes. The mixture was evaporated to dryness under reduced pressure and the remaining residue was dried at room temperature under vacuum to obtain 1.78 g (95%) of 1-methyl-2-(trimethylsilylthio)-imidazole with a melting point of 49°-52° C.

$^1$H NMR (CCl$_4$): 0.55 (s, 9H); 3.49 (s, 3H); 6.48 (d, 1H, J 2 Hz); 6.69 (d, 1H, J 2 Hz).

EXAMPLE 19

1-trimethylsilyl-3-trimethylsilylthio-1H-1,2,4-triazole 29.2 ml (0.14 mmole) of hexamethyldisilazane were added dropwise quickly to a refluxing suspension of 9.70 g (96 mmoles) of 3-mercapto-1H-1,2,4-triazole and 100 mg (0.25 mmole) of di-4-nitrophenyl N-(4-toluenesulfonyl)-phosphoramidate in 200 ml of dichloromethane, under a stream of dry nitrogen. The ammonia evolved was led into water by the nitrogen stream. By titration with 1 N sulfuric acid, it was established that the calculated amount of ammonia (96 mmoles) had been evolved within 1.25 hours and reflux was continued for another 0.5 hour. Then, the clear colorless solution was evaporated to dryness in a rotating film evaporator to obtain 23.1 g (98%) of 1-trimethyl-3-trimethylsilylthio-1H-1,2,4-triazole with a melting point of 90°-94° C.

$^1$H NMR (CCl$_4$): 0.52 (s, 9H); 0.55 (s, 9H); 7.52 (s, 1H).

EXAMPLE 20

1-phenyl-5-trimethylsilylthio-1H-tetrazole

Using the procedure of Example 19, 1.78 g (10 mmoles) of 1-phenyl-5-mercapto-1H-tetrazole in 50 ml of 1,2-dichloroethane was silylated with 2.60 ml (12.4 mmoles) of hexamethyldisilazane with 5 mg (0.03 mmole) of saccharin as the catalyst and the calculated amount of ammonia was collected within 20 minutes. Reflux was continued for another 10 minutes and then the mixture was evaporated to dryness and the residue was dried to obtain 2.58 g (103%) of 1-phenyl-5-trimethylsilylthio-1H-tetrazole with a melting point of 67°-68° C.

$^1$H NMR (CCl$_4$): 0.68 (s, 9H); 7.38-7.64 (m, 3H); 7.91-8.17 (m, 2H).

EXAMPLE 21

Trimethylsilyl-(4-chlorophenylthio)-silane

A mixture of 14.50 (0.10 mole) of 4-chlorothiophenol and 45 mg (0.25 mmole) of saccharin in a Claisen vessel was heated in an oil bath up to 120° C. while passing a stream of dry nitrogen over the mixture and 20.8 ml of hexamethyldisilazane (0.10 mole) were added dropwise quickly to the mixture. A precipitate was formed that disappeared again after heating for 10 minutes and the progress of the reaction was supervised by leading the ammonia evolved with the nitrogen stream into water and titrating with 1 N sulfuric acid. It was established that the calculated amount of ammonia had been evolved within 40 minutes and the product was isolated by fractionation under reduced pressure to obtain 19.81 g (91.5%) of trimethylsilyl-(4-chlorophenylthio)-silane with a boiling point of 82°-84° C. at 2.0 mm H.

EXAMPLE 22

Trimethyl-(4-methylphenylthio)-silane

A. Using the procedure of Example 21, 14.70 g (118 mmoles) of 4-methylthiophenol were silylated with 25 ml (120 mmoles) of hexamethyldisilazane using 40 mg (0.08 mmole) of tetraphenylimidodiphosphate as the catalyst and it was established that the silylation was completed within 1 hour. The product was isolated by distillation under vacuum to obtain 22.16 g (95.4%) of trimethyl-(4-methylphenylthio)-silane with a boiling point of 80.5°-82.0° C. at 2.5 mm Hg.

B. In a second run, 11.35 g (91.5 mmoles) of 4-methylthiophenol and 20.8 ml (100 mmoles) of hexamethyldisilazane were used with 200 mg (0.42 mmoles) of tetraphenylimidodiphosphate. With this amount of the catalyst, it was found that the reaction was already fully completed within 30 minutes and by distillation, trimethyl-(4-methylphenylthio)-silane was isolated in a yield of 84% with a boiling point of 79°-81° C. at 2.5 mm Hg.

EXAMPLE 23

4,6-dimethyl-2-(trimethylsilylthio)-pyrimidine 1.0 ml (4.8 mmoles) of hexamethyldisilazane was added to a refluxing mixture of 0.70 g (5.0 mmoles) of 4,6-dimethyl-2-mercaptopyrimidine, 10 mg (0.02 mmole) of tetraphenylimidodiphosphate and 25 ml of toluene and according to the procedure of Example 19, it was established that the calculated amount of ammonia had been evolved after refluxing for 1.5 hours. The mixture was then evaporated to dryness and the residue was dried to obtain 1.08 g (102%) of 4,6-dimethyl-2-(trimethylsilylthio)-pyrimidine.

$^1$H NMR (CCl$_4$): 0.43 (s, 9H); 2.32 (s, 6H); 6.63 (s, 1H).

EXAMPLE 24

2-methylamino-5-trimethylsilylthio-1,3,4-thiadiazole

To a refluxing solution of 298 mg (2.03 mmoles) of 2-methylamino-5-mercapto-1,3,4-thiadiazole and 2 mg (0.004 mmole) of tetraphenylimidodiphosphate in 10 ml of ethyl acetate, 0.42 ml (2.0 mmoles) of hexamethyldisilazane was added and by the procedure of Example 19, it was established that the evolution of ammonia came to an end after refluxing for 0.5 hours. At that time, 1 mmole of ammonia had been collected and reflux was continued for another 0.5 hour. Then, the solvent and other volatile materials were removed in a rotating film evaporator to obtain 434 mg (97%) of 2-methylamino-5-trimethylsilylthio-1,3,4-thiadiazole with a melting point of 80°-82° C.

$^1$H NMR (CCl$_4$): 0.60 (s, 9H); 2.90 (d, 3H, J 5.5 Hz); 5.85 (q, 1H, J 5.5 Hz).

EXAMPLE 25

Trimethyl-(4-bromophenylthio)-silane

Using the procedure of Example 21, 10.82 g (57.2 mmoles) of 4-bromothiophenol were silylated with 8.9 ml (42.6 mmoles) of hexamethyldisilazane with 25 mg (0.05 mmole) of di-4-nitrophenyl-N-(4-toluenesulfonyl)-phosphoramidate as the catalyst and the calculated amount of ammonia had been collected after reflux for 15 minutes. Fractionation under reduced pressure yielded 13.16 g (88.4%) of trimethyl-(4-bromophenylthio)-silane with a boing point of 87°-88° C. at 0.8 mm Hg and a n$_D$25 = 1.5652.

EXAMPLE 26

Trimethyl-(3,4-dichlorophenylthio)-silane

Using the procedure of Example 21, 8.45 mg (47.2 mmoles) of 3,4-dichlorothiophenol were silylated with 7.40 ml (35.4 mmoles) of hexamethyldisilazane with 22 mg (0.045 mmole) of tetraphenylimidodiphosphate as the catalyst and the calculated amount of ammonia had been evolved within 35 minutes. Fractionation under reduced pressure yielded 11.28 g (95.3%) of trimethyl-(3,4-dichlorophenylthio)-silane with a boiling point of 96°-97° C. at 0.8 mm Hg and $n_D25 = 1.5600$.

EXAMPLE 27

Trimethylsilyl 5-trimethylsilylthio-1H-tetrazolyl-1-acetate 0.6 ml of hexamethyldisilazane (2.9 mmoles) was added to a refluxing mixture of 318 mg (2.0 mmoles) of 5-mercapto-1H-tetrazolyl-1-acetic acid, 5.5 mg (0.03 mmole) of saccharin and 25 ml of toluene and after 2 hours of reflux, the evolution of ammonia came to an end. At that time, 2 mmoles of ammonia had been collected and the mixture was evaporated to dryness under reduced pressure. The residue was dried to obtain 0.60 g (100%) of trimethylsilyl 5-trimethylsilylthio-1H-tetrazolyl-1-acetate as a viscous oil. $^1$H NMR (CCl$_4$): 0.29 (s, 9H); 0.65 (s, 9H); 4.87 (s, 2H).

EXAMPLE 28

Trimethylsilyl 5-trimethylsilylthio-1,3,4-thiadiazolyl-2-acetate 0.9 ml (4.3 mmoles) of hexamethyldisilazane was added to a refluxing mixture of 0.44 g (2.5 mmoles) of 5-mercapto-1,3,4-thiadiazolyl-2-acetic acid, 5.0 mg (0.025 mmole) of saccharin and 30 ml of dichloromethane, and the calculated amount of ammonia (2.5 mmoles) had been evolved after refluxing for 1.5 hours. The mixture was then evaporated to dryness and the residue was dried under reduced pressure to obtain 0.80 g (100%) of trimethylsilyl 5-trimethylsilylthio-1,3,4-thiadiazolyl-2-acetate melting at 45°-49° C.

$^1$H NMR (CCl$_4$): 0.33 (s, 9H); 0.60 (s, 9H); 3.73 (s, 2H).

EXAMPLE 29

Trimethylsilyl benzoate

A. 15.6 ml of hexamethyldisilazane (0.075 mole) were added over 5 minutes to a refluxing solution of 12.2 g (0.1 mole) of benzoic acid and 90 mg (0.5 mmole) of saccharin in 30 ml of dichloromethane and by titration of the ammonia evolved, it was found that the calculated amount was produced in 40 minutes after starting the addition of the hexamethyldisilazane. The solvent was distilled off at normal pressure and the residue was vacuum distilled to yield 17.80 g (91.7%) of trimethylsilyl benzoate with a boiling point of 102°-104° C. at 13 mm Hg and $n_D25 = 1.4837$. In a run without a catalyst, refluxing had to be continued for 2.25 hours to evolve the calculated amount of ammonia. In both cases, a thick precipitate was formed after the addition of the hexamethyldisilazane which disappeared as the silylation proceeded.

B. The above experiment was repeated using 117 mg (0.5 mmole) of sodium saccharinate 2aq. instead of saccharin and the calculated amount of ammonia was evolved after refluxing for 40 minutes. Fractional distillation yielded 18.85 g (97.2%) of trimethylsilyl benzoate with a boiling point of 56°-57° C. at 0.5 mm Hg and $n_D25 = 1.4843$.

EXAMPLE 30

Trimethylsilyl trichloroacetate

A solution of 12.3 g (75 mmoles) of trichloroacetic acid in 30 ml of 1,2-dichloroethane was added dropwise over 10 minutes at room temperature to a mixture of 34 mg (0.18 mmole) of saccharin and 31.3 ml (150 mmoles) of hexamethyldisilazane while a stream of dry nitrogen was passed over the mixture whereby a precipitate was formed. Then the mixture was refluxed for 1.5 hours whereby the two-layer system present at the outset faded into a homogeneous solution and the calculated amount of ammonia was collected. Then dichloroethane was removed by distillation under normal pressure whereby a small amount of solid was separated in the cooler and vacuum distillation of the residue yielded 14.94 g (84.9%) of trimethylsilyl trichloroacetate with a boiling point of 63°-64° C. at 11 mm Hg and $n_D25 = 1.4360$.

EXAMPLE 31

Trimethylsilyl 2-trimethylsilyloxybenzoate 41.7 g (0.20 mole) of hexamethyldisilazane were added dropwise in 5 minutes to a mixture of 13.80 g (0.10 mole) of salicylic acid and 50 mg (0.10 mmole) of di-4-nitrophenyl N-(4-toluenesulfonyl)-phosphoramidate heated to 130° C. and the ammonia evolved was led into water by a dry stream of nitrogen which was passed over the reaction mixture. It was established by titration with 1 N sulfuric acid that the calculated amount of ammonia had been evolved within 45 minutes. Fractionation under reduced pressure yielded 27.86 g (98.8%) of trimethylsilyl 2-trimethylsilyloxybenzoate with a boiling point at 104°-105° C. at 1.5 mm Hg and $n_D25 = 1.4746$.

EXAMPLE 32

Ethyl trimethylsilyl malonate 20.8 ml (0.10 mmole) of hexamethyldisilazane were added dropwise quickly to a refluxing solution of 22.9 g (0.173 mole) of ethyl hydrogen malonate and 30 mg (0.17 mmole) of saccharin in 25 ml of dichloromethane under a stream of dry nitrogen and a two-layer system was obtained which faded into a homogeneous solution as the reaction proceeded. By titration of the ammonia evolved, it was established that the evolution of ammonia was completed after 1.5 hours and reflux was continued for another 0.5 hour. Then, the mixture was fractionated under reduced pressure to obtain 34.1 g (96.6%) of ethyl trimethylsilyl malonate boiling at 49.0°-50.5° C. at 0.4 mm Hg and $n_D26 = 1.4135$.

EXAMPLE 33

Trimethylsilyl 5-mercapto-1H-tetrazolyl-1-acetate

To a refluxing mixture of 0.30 g (1.86 mmoles) of 5-mercapto-1H-tetrazolyl-1-acetic acid, 0.5 ml (2.4 mmoles) of hexamethyldisilazane and 25 ml of 1,2-dichloroethane and 6.0 mg (0.012 mmole) of tetraphenylimidodiphosphate were added after reflux for 1 hour, 1 equivalent of ammonia had been evolved. The mixture was then evaporated to dryness under reduced pressure and the residue was dried to obtain 0.45 g (105%) of trimethylsilyl 5-mercapto-1H-tetrazolyl-1-acetate melting at 130°-33° C.

EXAMPLE 34

N,N'-bis-(trimethylsilyl)-urea 10 ml of hexamethyldisilazane (48 mmoles) were added to 2.4 g (40 mmoles) of urea and 73 mg (0.4 mmole) of saccharin in 15 ml of refluxing ethyl acetate and evolution of ammonia started immediately and was completed after refluxing for 20 minutes established by titration with 1 N HCl. The volatile material was evaporated under vacuum and the residue was vacuum dried to obtain 8.06 (99%) of N,N'-bis-(trimethylsilyl)-urea melting at 219°-222° C. Without the addition of saccharin as a catalyst, evolution of ammonia was slow and the reaction had to be carried out for at least 24 hours for completion.

EXAMPLE 35

N-trimethylsilyl-trichloroacetamide

A mixture of 16.24 g (0.10 mole) of trichloroacetamide, 15 mg (0.08 mmole) of saccharin, 25 ml of toluene and 15 ml (0.07 mole) of hexamethyldisilazane was placed in a preheated oil bath (120° C.) and refluxed for 30 minutes, after which evolution of ammonia was no longer detectable. The volatile materials were evaporated under vacuum and the residue was vacuum dried at 50° C. to obtain 22.58 g (96.3%) of crude N-trimethylsilyl-trichloroacetamide melting at 75°-85° C. and which dissolved clearly in petroleum ether.

EXAMPLE 36

N-trimethylsilylbenzamide 6.4 ml of hexamethyldisilazane (31 mmoles) were added to a refluxing mixture of 15 ml of toluene, 40 mg of saccharin (0.22 mmole) and 5.0 g of benzamide (41.3 mmoles) and the ammonia liberated was led into water by a stream of nitrogen passed over the reaction mixture. Titration with 1 N $H_2SO_4$ revealed that the calculated amount of ammonia was evolved in 15 minutes and solvent and excess hexamethyldisilazane were evaporated in vacuo to obtain 8.04 g (101%) of N-trimethylsilylbenzamide melting at 111°-115° C. The experiment was repeated without the addition of saccharin and it was found that 82% of the theoretical amount of ammonia was evolved in 15 minutes and 88% of it in 50 minutes.

EXAMPLE 37

N-trimethylsilyl-4-nitrobenzamide

A. 5.0 g of 4-nitrobenzamide (30.1 mmoles) was treated with 47 ml of hexamethyldisilazane (93% purity; 21 mmoles) in 20 ml of refluxing butyl acetate in the presence of 50 mg of saccharin (0.27 mmole) by the method of Example 18 and the theoretical amount of ammonia was evolved in 15 minutes. Evaporation of the volatile materials in vacuo gave 7.2 g of a pale brown residue of N-trimethylsilyl-4-nitrobenzamide (100%) melting at 130.5°-134.5° C.

B. 4.5 ml of hexamethyldisilazane (22 mmoles) were added to a refluxing mixture of 5.0 g (30.1 mmoles) of 4-nitrobenzamide, 100 mg (0.5 mmole) of 1,8-naphthalimide and 20 ml of butyl acetate and the calculated amount of ammonia was evolved after refluxing for 35 minutes. The same experiment without catalyst was carried out and only 16% of the theoretical amount of ammonia was evolved after refluxing for 15 minutes. After refluxing for 1 hour, 83% of that amount of evolved.

EXAMPLE 38

N-trimethylsilyl-α,α-dimethylpropionamide 7.7 ml (37 mmoles) of hexamethyldisilazane were added to 5.0 g (49.5 mmoles) of α,α-dimethylpropionamide and 10 mg (0.05 mmole) of saccharin in 15 ml of refluxing tolune over 15 minutes and after refluxing for 45 minutes, the evolution of ammonia had stopped completely. Evaporation and drying in vacuo yielded 8.04 g (98%) of N-trimethylsilyl-α,α-dimethylpropionamide melting at 101°-105.5° C. According to NMR analysis, the purity of the product was 92%.

EXAMPLE 39

N-trimethylsilylacetamide

A mixture of 5.90 (0.1 mole) of acetamide and 55 mg (0.3 mmole) of saccharin was heated to 130° C. and 15.6 ml (0.075 mole) of hexamethydisilazane were added over 3 minutes. By the method of Example 1A, it was found that the calculated amount of ammonia was evolved in 35 minutes after starting the addition of the hexamethyldisilazane. Refluxing was continued for 10 minutes and excess hexamethyldisilazane was evaporated under reduced pressure. The solid residue was dried under vacuum to obtain 12.80 g (97.7%) of N-trimethylsilylacetamide of more than 95% purity according to MNR analysis.

EXAMPLE 40

N-trimethylsilylurethane 15.6 ml of hexamethyldisilazane (0.075 mole) were added over 2 minutes to a refluxing mixture of 8.9 g (0.1 mole) of urethane, 183 mg (1 mmole) of saccharin and 10 ml of toluene and the theoretical amount of ammonia was evolved in 30 minutes. Refluxing was continued for 15 minutes and the solvent and excess hexamethyldisilazane were removed under reduced pressure. The residue was vacuum distilled to obtain 15.6 g (96.9%) of N-trimethylsilylurethane boiling at 73° C. at 12 mm Hg and $n_D25 = 1.4268$.

EXAMPLE 41

N,N'-bis-(trimethylsilyl)-malonamide

A. 7.5 ml (36 mmoles) of hexamethyldisilazane were added to a refluxing mixture of 3.06 g (0.03 mmole) of malonamide, 18.3 mg (0.1 mmole) of saccharin, 50 ml of ethyl acetate and 5 ml of pyridine and by titrating with 1 N sulfuric acid the ammonia evolved, it was found that 30 mmoles were expelled after refluxing for one hour. Volatile material was vacuum evaporated and the residue, which crystallized upon standing, was dried in vacuo to obtain 7.32 g (99%) of N,N'-bis-(trimethylsilyl)-malonamide melting at 72°-76° C. NMR Spectrum ($CDCl_3$): Δ0.24 (s, 18H); 3.20 (s, 2H); 6.5 (broad, 2H).

B. A similar run using 30 ml of butyl acetate as the solvent required refluxing for 15 minutes to evolve the calculated amount of ammonia and the melting point of the residue was 71°-80° C. for a yield of 6.72 g (91%).

EXAMPLE 42

N-trimethylsilylcaprolactam

A mixture of 22.6 g (0.2 mole) of caprolactam, 0.73 g (4 mmoles) of saccharin and 40 ml (0.19 mole) of hexamethyldisilazane was refluxed for 3.5 hours after which time ammonia evolution could no longer be detected. The dark brown reaction mixture was vacuum distilled to yield 21.64 g (58.5%) of N-trimethylsilylcaprolactam boiling at 103°–106° C. at 12 mm Hg.

EXAMPLE 43

Trimethylsilylsaccharin 2 ml (9.6 mmoles) of hexamethyldisilazane were added to a refluxing mixture of 1.83 mg (10 mmoles) of saccharin, 10 mg (0.02 mmole) of di-4-nitrophenyl N-(4-toluenesulfonyl)-phosphoramidate and 20 ml of acetonitrile under dry nitrogen and the ammonia evolved was led into water by the nitrogen stream and was titrated with 1 N sulfuric acid. The calculated amount of ammonia was evolved within 0.5 hour and the solvent and other volatile materials were removed by evaporation in a rotating film evaporator. Then, the residue was dried under vacuum to obtain 2.50 g (98%) of trimethylsilylsaccharin melting at 90°–92° C.

$^1$H NMR (CCl$_4$): 0.53 and 0.57 (two singulets, together 9H); 7.66–8.13 (m, 4H).

$^{13}$C NMR (CDCl$_3$, 20 MHz, internal standard TMS): −1.2; −0.4; 1.8; 120.5; 121.4; 123.6; 124.8; 133.3; 133.8; 134.8.

EXAMPLE 44

N-trimethylsilylbenzenesulfonamide 15.6 ml of hexamethyldisilazane (75 mmoles) were added to a refluxing suspension of 15.72 g (0.1 mole) of benzenesulfonamide and 18 mg (0.1 mmole) of saccharin in 45 ml of ethyl acetate under nitrogen and the nitrogen was passed through water to determine the amount of ammonia evolved. By titrating with 1 N H$_2$SO$_4$, it was found that the calculated amount of ammonia was set free in 25 minutes and the residue of N-trimethylsilylbenzensulfonamide obtained after evaporating the volatile materials in vacuo melted at 62°–63° C.

EXAMPLE 45

N-trimethylsilylmethanesulfonamide 5.1 ml of hexamethyldisilazane (24.5 mmoles) were added to a refluxing mixture of 3.0 g (31.6 mmoles) of methanesulfonamide, 20 mg (0.11 mmole) of saccharin and 15 ml of toluene while a stream of nitrogen passed over the reaction mixture to expel the ammonia evolved, which was absorbed in water and titrated with 1 N H$_2$SO$_4$. It was found that after refluxing for 20 minutes the calculated amount of ammonia was evolved. The solvent and excess hexamethyldisilazane were evaporated in vacuo and the solid residue was vacuum dried to obtain 5.22 g (99.5%) of N-trimethylsilylmethanesulfonamide melting at 69°–74.5° C. The experiment was repeated without the addition of saccharin and the calculated amount of ammonia was evolved in 35 minutes. Workup as described above yielded 5.25 g (100%) of N-trimethylsilylmethansulfonamide melting at 68°–72.5° C.

EXAMPLE 46

N-trimethylsilylthioacetamide 17.2 ml of hexamethyldisilazane (82 mmoles) were added over 10 minutes to a refluxing mixture of 11.3 g (0.15 mole) of thioacetamide, 0.14 g (0.75 mmole) of saccharin and 50 ml of toluene and the ammonia produced in the reaction was passed by a stream of dry nitrogen into water and titrated with 1 N HCl. It was found that after refluxing for 1.5 hours after the addition of the hexamethyldisilazane the calculated amount of ammonia was evolved. Toluene and the excess of hexamethyldisilazane were distilled off at normal pressure and the residue was vacuum distilled to yield 13.12 g (59.2%) of N-trimethylsilylthioacetamide boiling at 97°–99° C. at 0.7 mm Hg.

EXAMPLE 47

N-trimethylsilyl diphenylphosphoramidate 3.2 ml of hexamethyldisilazane (15.4 mmoles) were added to 5.0 g (20.1 mmoles) of diphenylphosphoramidate and 36 mg (0.20 mmole) of saccharin in 35 ml of refluxing toluene and a stream of nitrogen was led over the reaction mixture and the ammonia evolved was absorbed in water and titrated with 1 N H$_2$SO$_4$. The calculated quantity of ammonia was liberated in 15 minutes. Refluxing was continued for 10 minutes and the solvent evaporated in vacuo to obtain 6.69 g of N-trimethylsilyl diphenylphosphoramidate melting at 83°–86.5° C. The experiment was repeated without the addition of saccharin and after refluxing for 15 minutes, 26% of the calculated quantity of ammonia was liberated and 69% after refluxing for 1 hour.

EXAMPLE 48

N,O,O-tris-(trimethylsilyl)-DL-serine 52.2 ml (0.25 mole) of hexamethyldisilazane were added to a refluxing suspension of 10.50 g (0.1 mole) of DL-serine, 30 ml of toluene and 91 mg (0.5 mmole) of saccharin and a stream of dry nitrogen was led over the reaction mixture and passed through water to determine the amount of ammonia evolved. By titrating with 1 N H$_2$SO$_4$, it was found that three equivalents of ammonia were evolved in three hours (two equivalents were evolved after one hour). The toluene and the excess of hexamethyldisilazane were evaporated in vacuo and the residue was vacuum distilled to give 22.92 g (76.2%) of N,O,O-tris-(trimethylsilyl)-DL-serine boiling at 87°–89° C. at 0.5–0.6 mm Hg and n$_D$25 = 1.4213.

EXAMPLE 49

Trimethylsilyl d,l-α-trimethylsilylaminopropionate

A mixture of 8.90 g (0.1 mole) of d,l-alanine and 50 mg (0.1 mmole) of di-4-nitrophenyl N-4-toluenesulfonylphosphoramide was placed in a preheated (140° C.) oil bath and 41.6 ml (0.2 mole) of hexamethyldisilazane were added. After refluxing for 2 hours, the calculated amount (0.1 mole) of ammonia was evolved as was established by leading it into water and titrating with 1 N H$_2$SO$_4$. The colorless solution was vacuum distilled to yield 20.72 g (88.9%) of trimethylsilyl d,l-α-trimethylsilylaminopropionate boiling at 78°–81° C. 18 mm Hg and n$_D$25 = 1.4145.

EXAMPLE 50

N-trimethylsilylsuccinimide

A. 31.5 ml of hexamethyldisilazane (0.15 mmole) were added to a refluxing suspension of a mixture of 50 ml of toluene and 19.80 g (0.20 mole) of succinimide and 458 mg of saccharin (2.5 mmoles) and refluxing was continued for 2 hours. Fifteen minutes after the addition of the silylating agent, a clear, light yellow solution was obtained which turned brown when refluxing was continued. The reaction mixture was cooled, filtered and after evaporation of the solvent, the residue was vacuum distilled to obtain 31.04 g (90.8%) of N-trimethylsilylsuccinimide boiling at 86°–88° C. at 1.3 mm Hg.

B. 15.6 ml (0.075 mole) of hexamethyldisilazane were added dropwise over a few minutes to a refluxing suspension of 9.90 g (0.1 mole) of succinimide and 0.24 g (0.5 mmole) of di-4-nitrophenyl N-4-toluenesulfonylphosphoramidate in 50 ml of dichloromethane and a stream of nitrogen was led over the reaction mixture to pass the ammonia evolved into water. The progress of the reaction was established by titration of the ammonia evolved and it was found that after refluxing for 1.5 hours, the production of ammonia was completed. 90% of the theoretical amount of ammonia had been evolved and refluxing was continued for another 2 hours. Then the solvent was removed by distillation at normal pressure and fractionation under reduced pressure yielded 15.36 g (89.8%) of N-trimethylsilylsuccinimide boiling at 118°–119° C. at 18 mm Hg and $n_D25 = 1.4745$.

EXAMPLE 51

N-trimethylsilylphthalimide

A mixture of 36.8 g (0.25 mole) of phthalimide, 0.92 g (5 mmoles) of saccharin and 75 ml (0.36 mole) of hexamethyldisilazane was placed in an oil bath that was preheated to 120° C. and evolution of ammonia started immediately. A clear solution was obtained after 30 minutes and after that time, the mixture was refluxed for 60 minutes. Volatile materials were evaporated under vacuum and 50 ml of petroleum ether (b.p. 80°–110° C.) were added. The mixture was evaporated again to dryness and the nearly colorless 54.89 g (100%) of N-trimethylsilylphthalimide melted at 66°–68° C., which is in good agreement with literature data for N-trimethylsilylphthalimide. The alleged structure of the compound was also confirmed by its NMR spectrum.

EXAMPLE 52

N-trimethylsilylimidazole 31.5 ml (0.15 mole) of hexamethyldisilazane were added dropwise over the course of 45 minutes to 13.62 g (0.2 mole) of imidazole and 28 mg (0.15 mmoles) of saccharin heated to 100° C. and during this addition, the bath temperature was raised from 100° to 140° C. After addition of the hexamethyldisilazane, the mixture was stirred for 30 minutes at a bath temperature of 140° C. Excess hexamethyldisilazane was evaporated under reduced pressure and the residue was vacuum distilled to obtain 22,25 g (79.5%) of N-trimethylsilylimidazole boiling at 103°–105° C. at 22 mm Hg and $n_D23.5° = 1.4740$.

EXAMPLE 53

1,3-bis-(trimethylsilyl)-5,5-dimethylhydantoin 80 ml of hexamethyldisilazane (0.38 mole) were added over 30 minutes to a refluxing suspension of 50 ml of toluene, 40 mg (0.22 mmole) of saccharin and 38.45 g (0.30 mole) of 5,5-dimethylhydantoin and evolution of ammonia started immediately. When half of the hexamethyldisilazane had been added, all solids had gone into solution and after the addition of the hexamethyldisilazane, reflux was continued for 1 hour. Toluene was distilled off and the residue was vacuum dried at 45° C. to obtain 79.0 g (97%) of 1,3-bis-(trimethylsilyl)-5,5-dimethylhydantoin melting at 46°–49° C. According to NMR analysis, the purity of the compound was 91%.

EXAMPLE 54

N-trimethylsilyl-2-oxazolidone

A mixture of 25 ml of toluene, 10 mg of saccharin (0.05 mmole) and 10.0 g of 2-oxazolidone of 94% purity (108 mmoles) was heated to reflux, and 14.3 ml of hexamethyldisilazane (69 mmoles) were added over 10 minutes. Refluxing was continued for 1 hour and evolution of ammonia had stopped completely after that period of time. The solvent was evaporated in vacuo and the residue was vacuum distilled to give 14.6 g (85%) of N-trimethylsilyl-2-oxazolidone boiling at 62° C. at 0.2 mm and $n_D23 = 1.4529$.

EXAMPLE 55

1-trimethylsilyl-1,2,4-triazole 23.4 ml (0.11 mole) of hexamethyldisilazane were added to a mixture consisting of 10.35 g (0.15 mole) of 1,2,4-triazole and 127 mg (0.75 mmole) of saccharin heated to 126° C. and evolution of ammonia started immediately. After refluxing for 30 minutes, the calculated amount of ammonia was evolved as determined by the method described in Example 1A. Vacuum distillation yielded 19.37 g (91.6%) of 1-trimethylsilyl-1,2,4-triazole boiling at 76.5°–78.0° C. at 12 mm Hg and $n_D25 = 1.4592$.

EXAMPLE 56

Trimethylsilyl 6-aminopenicillanate

A. 1 ml of hexamethyldisilazane was added (4.8 mmole) to a refluxing suspension of 1.08 g (5.0 mmoles) of 6-aminopenicillanic acid and 20 mg (0.11 mmole) of saccharin in 20 of dichloromethane. After refluxing for 0.5 hour, a substantially clear solution was obtained indicating that the dichloromethane-insoluble 6-aminopenicillanic acid was converted into the soluble trimethylsilyl ether. Omission of the saccharin prolonged the reaction time to 4 hours.

B. 1.0 ml (4.8 mmoles) of hexamethyldisilazane was added to a suspension of 1.08 g (5.0 mmoles) of 6-aminopenicillanic acid, 30 mg (0.11 mmole) of dimethyl N-trichloroacetylphosphoramidate and 20 ml of refluxing dichloromethane and a clear solution, indicating that the dichloromethane-insoluble 6-aminopenicillanic acid was converted into the soluble trimethylsilyl ester, was obtained after refluxng for 40 minutes.

C. A suspenion consisting of 1.08 g (5.0 mmoles) of 6-aminopenicillanic acid, 20 mg (0.11 mmole) of saccharin and 15 ml of chloroform (alcohol-free) was heated to reflux and 0.75 ml of hexamethyldisilazane (3.6 mmole) was added to it. After refluxing for 20 minutes, a substantially clear solution was obtained, indicating that the dichloromethane-insoluble 6-aminopenicillanic acid was converted into the soluble trimethylsilyl ester. Ommission of the saccharin prolonged the reaction time to 1.5 hours.

D. 1.0 ml (4.8 mmoles) of hexamethyldisilazane was added to a suspension of 1.08 g (5.0 mmoles) of 6-aminopenicillanic acid and 53 mg (0.11 mmole) of di-4-nitrophenyl N-trichloroacetylphosphoramidate in 20 ml of refluxing dichloromethane and a clear solution, indicating that the dichloromethane-insoluble 6-aminopenicillanic acid was converted into the soluble trimethylsilyl ester, was obtained after refluxing for 25 minutes.

EXAMPLE 57

Trimethylsilyl 6-trimethylsilylaminopenicillanate 2.5 ml (12 mmoles) of hexamethyldisilazane were added to a refluxing suspension of 0.86 g (4 mmoles) of 6-aminopenicillanic acid, 12 mg (0.07 mmole) of saccharin and 25 ml of chloroform and after refluxing for 20 minutes, a clear solution was obtained. After refluxing for 2 hours, volatile material was evaporated under vacuum at a bath temperature of 40° C. The clear, colorless oil that remained was dissolved in 4 ml of dry carbon tetrachloride and from the NMR spectrum of this solution, it could be concluded that 90% trimethylsilyl 6-trimethylsilylaminopenicillanate was present.

EXAMPLE 58

Trimethylsilyl 6-D-(—)-α-aminophenylacetamido-penicillanate 3.49 g of 6-D-(—)-α-aminophenylacetamido-penicillanic acid (10 mmoles) were suspended in 35 ml of dichloromethane and 92 mg of saccharin (0.5 mmole) were added thereto. The mixture was heated to reflux and 1.55 ml (7.4 mmoles) of hexamethyldisilazane were added. A clear, colorless solution was obtained after refluxing for 25 minutes indicating that the dichloromethane-insoluble penicillanic acid derivative was converted into the soluble trimethylsilyl ester. A parallel run in which no saccharin was added gave a clear solution only after refluxing for 50 minutes.

EXAMPLE 59

Trimethylsilyl 6-(D-(—)-α-amino-p-trimethylsilyloxy-phenylacetamido)-penicillanate 0.7 ml (3.4 mmoles) of hexamethyldisilazane were added to a refluxing suspension of 0.73 g (2 mmoles) of 6-(D-(—)-α-amino-p-hydroxyphenylacetamido)-penicillanic acid and 5 mg (0.027 mmole) of saccharin in 15 ml of dichloromethane and the clear solution that was obtained after refluxing for 20 minutes was refluxed for one hour more. The solvent was evaporated in vacuo and the residue was vacuum dried. The 1.15 g of solid residue was the 0,0-bis-(trimethylsilyl) derivative of the starting material according to the NMR spectrum. In a parallel run without the addition of saccharin, it took two and a half hours of refluxing to obtain a clear solution.

EXAMPLE 60

Trimethylsilyl 6-trimethylsilylaminopenillanate-1-oxide

Using the procedure of Example 72, 465 mg (2.0 mmoles) of 6-aminopenicillanic acid-1-oxide were silylated in 20 ml of chloroform with 1.6 ml (7.7 mmoles) of hexamethyldisilazane using 1.0 mg (0.002 mmole) of tetraphenyl imidodiphosphate as the catalyst. The calculated amount of ammonia was evolved in 1.5 hours and after refluxing for 1.75 hours, the mixture was evaporated to dryness in a rotating film evaporator. After addition of 10 ml of dry carbon tetrachloride, evaporation to dryness was repeated and the 0.81 g of trimethylsilyl 6-trimethylsilylaminopenillanate-1-oxide was dissolved in carbon tetrachloride.

$^1$H NMR: 0.11 (s, 9H); 0.33 (s, 9H); 1.17 (s, 3H); 1.65 (s, 3H); 2.36 (d, 1H, J 12.8 Hz); 4.45 (s, 1H); 4.45, 4.76 and 4.72 (dd and s, 2H, J 4.5 Hz).

EXAMPLE 61

Trimethylsilyl 6-trimethylsilylaminopenicillanate-1,1-dioxide

Using the procedure of Example 60, 506 mg (2.0 mmoles) of 6-aminopenicillanic acid-1,1-dioxide containing 6% by weight of water were silylated with 1.9 ml (9.1 mmoles) of hexamethyldisilazane in 20 ml of chloroform using 1.0 mg (0.002 mmole) of di-4-nitrophenyl N-trichloroacetylphoshoramidate as the catalyst. The calculated amount of ammonia (3.6 mmoles) was evolved in 3.25 hours and the solvent was then removed under reduced pressure. By the $^1$H NMR Spectrum of the 0.76 g residue, it was established that a complete disilylation had been effected.

$^1$H NMR (CCl$_4$): 0.14 (s, 9H); 0.34 (s, 9H); 1.33 (s, 3H); 1.53 (s, 3H); 2.27 (d, 1H, J 14 Hz); 4.28 (s, 1H); 4.47 (d, 1H, J 4.5 Hz); 4.60 and 4.85 (dd, 1H, J 4.5 and 14 Hz).

EXAMPLE 62

Trimethylsilyl 7-amino-3-methyl-3-cephem-4-carboxylate

A. 1.25 ml of hexamethyldisilazane (6 mmoles) were added to a refluxing suspension of 1.07 g (5.0 mmoles) of 7-amino-3-methyl-3-cephem-4-carboxylic acid in 20 ml of chloroform (p.a. quality stabilized with ethanol) and 20 mg of saccharin (0.11 mmole) while a gentle stream of dry nitrogen led over the reaction mixture helped to expel the ammonia produced and maintained the system under anhydrous conditions. After refluxing for 25 minutes, a clear, yellowish solution was obtained indicating that the chloroform-insoluble carboxylic acid was converted into the soluble trimethylsilyl ester. Omission of the saccharin in the reaction mixture prolonged the reaction time to 3.5 hours.

B. By the method of Example 62A, a clear solution was obtained after refluxing a mixture of 20 ml of dichloromethane (alcohol-free), 1.07 g (5.0 mmoles) of 7-amino-3-methyl-3-cephem-4-carboxylic acid, 1.05 ml (5 mmoles) of hexamethyldisilazane and 20 mg (0.11 mmole) of saccharin for 10 minutes. The same experiment with only 6.1 mg (0.03 mmole) of saccharin needed 20 minutes' reflux to give a clear solution and without saccharin, the reaction time was 2.5 hours.

C. 0.75 ml (3.6 mmoles) of hexamethyldisilazane were added to a refluxing suspension of 1.07 g (5.0 mmoles) of 7-amino-3-methyl-3-cephem-4-carboxylic acid, 20 ml of dichloromethane and 20 mg (0.11 mmole) of saccharin and after refluxing for 30 minutes, a clear solution was obtained. A parallel run without saccharin took 3.5 hours to obtain a clear solution.

D. 1.05 ml (5.0 mmoles) of hexamethyldisilazane was added to a refluxing suspension of 1.50 g (7.0 mmoles) of 7-amino-3-methyl-3-cephem-4-carboxylic acid, 20 ml of dichloromethane and 82 mg (0.5 mmole) of trichloroacetamide and a clear solution was obtained after refluxing for 50 minutes. Without trichloroacetamide added, the time required to obtain a clear solution was 210 minutes.

E. 10 mg (0.1 mmole) of sulfamide and 0.75 ml (3.6 mmoles) of hexamethyldisilazane were added to a refluxing suspension of 1.07 g (5 mmoles) of 7-amino-3-methyl-3-cephem-4-carboxylic acid in 20 ml of dichloromethane and after refluxing for 2 hours, a clear solution was obtained. With omission of the sulfamide, it took 210 minutes to obtain a clear solution.

F. 0.75 ml (3.6 mmoles) of hexamethyldisilazane was added to a refluxing mixture of 25 ml of dichloromethane, 1.07 g (5 mmoles) of 7-amino-3-methyl-3-cephem-4-carboxylic acid and 26 mg (0.11 mmole) of N,N'-bis-(trimethylsilyl)-sulfamide and after refluxing for 2 hours, a clear solution was obtained. The same experiment without the addition of N,N'-bis-(trimethylsilyl)-sulfamide needed 210 minutes' reflux to get a clear solution.

G. By the method of Example 62F, the reaction took 35 minutes when 41.4 mg (0.15 mmole) of N-benzoyl-benzenesulfonamide were used as a catalyst.

H. By the method of Example 62F, the reaction took 135 minutes when 54.8 mg (0.15 mmole) of N-(2-methoxy-1-naphthoyl)-4-toluenesulfonamide were used as a catalyst.

I. By the method of Example 62F, the reaction took 150 minutes when 42.8 mg (0.16 mmole) of N-(2-methoxy-1-naphthoyl)-methanesulfonamide were used as a catalyst.

J. 528 (3.28 mmoles) of hexamethyldisilazane were added to a refluxing suspension of 1.08 g (5.0 mmoles) of 7-amino-3-methyl-3-cephem-4-carboxylic acid, 10 mg (0.05 mmole) of saccharin and 20 ml of dichloromethyane and the clear solution obtained after refluxing for one hour was evaporated to dryness. The residue was dried at room temperature under vacuum and 1.48 g of product was analyzed by quantitative NMR analysis using an internal standard technique to ascertain that the yield of trimethylsilyl 7-amino-3-methyl-3-cephem-4-carboxylate, calculated on the trimethylsilyl ester peak, was 93%. Only a trace amount of trimethylsilyl 3-methyl-7-trimethylsilylamino-3-cephem-4-carboxylate could be detected in the NMR spectrum.

EXAMPLE 63

Trimethylsilyl 7-trimethylsilylamino-3-methyl-3-cephem-4-carboxylate

A. Di-4-nitrophenyl N-4-toluenesulfonyl-phosphoramidate 12 mg (0.024 mmole) were added to 40 ml of chloroform (pro analyzse quality containing ethanol) and the mixture was refluxed for half an hour to destroy any active hydrogen atoms-containing impurities present. The ammonia evolved during this period was driven off by leading a gentle stream of dry nitrogen over the mixture and then, 1.07 g (5.0 mmoles) of 7-amino-3-methyl-3-cephem-4-carboxylic acid was added. Refluxing was continued under the same conditions, but the stream of nitrogen now was led into water to absorb the ammonia evolved which was titrated with 0.1 N sulfuric acid. A clear solution was obtained after refluxing for 10 minutes (25 ml of the sulfuric acid solution was used then) and 50 ml of the sulfuric acid solution, indicative of complete disilylation, were used after refluxing for 35 minutes.

B. A mixture consisting of 0.80 g (3.7 mmoles) of 7-amino-3-methyl-3-cephem-4-carboxylic acid, 1.87 ml (11.6 mmoles) of hexamethyldisilazane, 8.8 mg (0.48 mmole) of saccharin and 20 ml of chloroform was heated to reflux and a clear solution was obtained after 10 minutes. After refluxing for 2 hours, volatile material was evaporated under vacuum (bath temperature 50° C.) and the solid residue was dissolved in 5 ml of carbon tetrachloride. From the NMR spectrum of this solution, it could be concluded that the N,O-disilylated derivative was present for 80% (by comparing the ratio of the N-trimethylsilyl and O-trimethylsilyl signals).

EXAMPLE 64

Trimethylsilyl 3-methyl-7-phenylacetamido-3-cephem-B 4-carboxylate-1-oxide

A. 1.25 ml (6.0 mmoles) of hexamethyldisilazane was added to a refluxing suspension of 1.4 g (4 mmoles) of 3-methyl-7-phenyl-acetamido-3-cephem-4-carboxylic acid-1-oxide in 25 ml of dichloromethane and a clear solution, indicative of complete silylation, was obtained after refluxing for 30 minutes.

B. The experiment was repeated with 13 mg (0.04 mmole) of ditosylamine added as a catalyst and a clear solution was obtained after refluxing for 8 minutes.

C. Using 74.8 mg (0.66 mmole) of 2,2,2-trifluoroacetamide as a catalyst, a clear solution was obtained after refluxing for 15 minutes.

D. A mixture of 1.083 g (3.1 mmoles) of 3-methyl-7-phenylacetamido-3-cephem-4-carboxylic acid-1-oxide, 42 mg (0.15 mmoles) of N-benzoyl-4-toluenesulfonamide and 25 ml of dichloromethane was heated to reflux, 0.57 ml (2.73 mmoles) of hexamethyldisilazane was added. Refluxing was continued for 5 minutes, after which time a clear, slightly brown solution was obtained. A parallel run in which the catalyst was omitted gave a clear solution after refluxing for 45 minutes.

E. 0.5 ml (2.4 mmoles) of hexamethyldisilazane was added to a refluxing mixture of 1.04 g (3.0 mmoles) of 3-methyl-7-phenylacetamido-3-cephem-4-carboxylic acid-1-oxide, 14.5 mg (0.3 mmole) of formamide and 30 ml of dichloromethane and a clear solution was obtained after refluxing for 45 minutes. In a parallel run in which the formamide was omitted, refluxing for 75 minutes was necessary to obtain a clear solution.

EXAMPLE 65

Trimethylsilyl 7-phenylacetamido-3-methyl-3-cephem-4-carboxylate-1-α-oxide

The trimethylsilyl 7-phenylacetamido-3-methyl-3-cephem-4-carboxylate 1-α-oxide was prepared by refluxing for 30 minutes a mixture of 0.17 g (0.5 mmole) of 7-phenylacetamido -3-methyl-3-cephem-4-carboxylic acid-1-α-oxide, 0.88 mg (0.005 mmole) of saccharine, 0.065 ml (0.31 mmole) of hexamethyldisilazane and 5 ml of deuterochloroform. According to the $^1$H NMR spectrum, the product had been formed quantatively.

$^1$H NMR (CDCl$_3$): 0.33 (s, 9H); 2.18 (s, 3H); 3.33 and 3.98 (ABq, 2H, J 16.5 Hz); 3.58 (s, 2H); 4.47 (d, 1H, J 4.5 Hz); 5.29 and 5.42 (dd, 1H, J 4.5 and 8 Hz); 7.13 (d, 1H, J 8 Hz); 7.29 (s, 5H).

EXAMPLE 66

Trimethylsilyl 7-formamido-3-methyl-3-cephem-4-carboxylate -1-oxide 0.62 ml (3.0 mmoles) of hexamethyldisilazane was added to a refluxing boiling suspension of 1.34 g (5.0 mmoles) of 7-formamido-3-methyl-3-cephem-4-carboxylic acid-1-oxide (96%), 5 mg (0.01 mmole) of tetraphenyl imidodiphosphate and 50 ml of dichloromethane and the calculated amount of ammonia was evolved in 80 minutes. After evaporation under reduced pressure of the volatile materials and drying under vacuum at room temperature, 1.63 g (99%) of trimethylsilyl 7-formamido-3-methyl-3-cephem-4-carboxylate-1-oxide as a solid of light-yellow color was obtained.

The characterization of the product was carried out as follows: a mixture of 106 mg of 7-formamido-3-methyl-3-cephem-4-carboxylic acid-1-oxide, 0.5 mg of saccharin, 3 ml of deuterochloroform and 0.05 ml of hexamethyldisilazane was refluxed for 1 hour and from the $^1$H NMR spectrum of the solution thus prepared, it was established from the integration ratio between the trimethyl signal and the 7-proton signal that the silylation had proceeded quantatively.

$^1$H NMR (CDCl$_3$): 0.32 (s, 9H); 2.16 (s, 3H); 3.23 and 3.68 (ABq, 2H, J 18 Hz); 4.53 (d, 1H, J 4.5 Hz); 5.97 and 6.11 (dd, 1H, J 4.5 and 9.8 Hz); 7.20 (d, 1H, J 9.8 Hz); 8.31 (s, 1H).

EXAMPLE 67

Trimethylsilyl 7-phenylacetamido-3-(1-methyl-1H-tetrazolyl-1-thio)-methyl-3-cephem-4-carboxylate-1-oxide Using the procedure of Example 75, 115 mg (0.25 mmole) of 7-phenylacetamido-3-(1-methyl-1H-tetrazolyl-5-thio)-methyl-3-cephem-4-carboxylic acid-1-oxide in 2 ml of deuteroform were silylated in 1.5 hours with 0.10 ml (0.48 mmole) of hexamethyldisilazane of using 0.048 mg (0.00026 mmole) of saccharin as the catalyst.

$^1$H NMR (CDCl$_3$): 0.33 (s, 9H); 3.54 (s, 2H); 3.25, 3.58, 3.88, 4.21 (ABq. 2H, J 19 Hz); 3.83 (s, 3H); 4.06, 4.29, 4.43, 4.66 (ABq. 2H, J 13 Hz); 4.44 (d, 1H, J 4.5 Hz); 5.99 (dd, 1H, J 4.5 and 10 Hz); 6.82 (d, 1H, J 10 Hz); 7.27 (s, 5H).

EXAMPLE 68

Bis-(trimethylsilylation) of 7-phenylacetamido-3-(1H-1,2,3-triazolyl-5-thio)-methyl-3-cephem-4-carboxylic acid-1-oxide Using the procedure of Example 76, 130 mg (0.29 mmole) of 7-phenylacetamido-3-(1H-1,2,3-triazolyl-5-thio)-methyl-3-cephem-4-carboxylic acid-1-oxide were converted into its bis (trimethylsilyl)-derivative by refluxing in 2 ml of deuterochloroform for 1 hour with 0.10 ml (0.48 mmole) of hexamethyldisilazane in the presence of 1.0 mg (0.002 mmole) of di-4-nitrophenyl N-trichloroacetylphosporamidate as the catalyst. From the NMR spectrum, it could be concluded that the product consisted of a mixture of two isomers differing as to the position of the trimethylsilyl group in the triazole ring.

$^1$H NMR (CDCl$_3$): 0.25 and 0.28 (2s, together 9H); 0.49 and 0.53 (2s, together 9H); about 3.2–4.7 (m, 7H); 5.95 (dd, 1H, J 4.5 and 9 Hz); 6.82 and 6.98 (2d, together 1H, in both J 9 Hz); 7.28 (s, 5H); 7.65 and 7.85 (2s, together 1H).

EXAMPLE 69

Trimethylsilyl 3-acetoxymethyl-7-amino-3-cephem-4-carboxylate 0.63 ml (3.0 mmoles) of hexamethyldisilazane were added to a refluxing suspension of 0.82 g (3.0 mmoles) of 3-acetoxymethyl-7-amino-3-cephem-4-carboxylic acid in 15 ml of dichloromethane and 11 mg of saccharin (0.06 mmole) and a clear solution, indicating that the chloroform-insoluble carboxylic acid was converted into the soluble trimethylsilyl ester, was obtained after refluxing for 10 minutes. The same experiment without the addition of saccharin was also carried out and refluxing had to be continued for 50 minutes to obtain a clear solution.

EXAMPLE 70

Trimethylsilyl 7-trimethylsilylamino-3-acetoxy-methyl-3-cephem-4-carboxylate 2.5 ml (12 mmoles) of hexamethyldisilazane were added to a refluxing suspension of 1.08 g (4 mmoles) of 3-acetoxymethyl-7-amino-3-cephem-4-carboxylic acid, 15 mg (0.08 mmole) of saccharin and 25 ml of chloroform and the mixture, which became clear after 10 minutes, was refluxed for 2 hours. After evaporation of the solvent and excess hexamethyldisilazane under vacuum at a bath temperature of 40° C., a brown, oily residue was obtained. This was dissolved in 4 ml of dry carbon tetrachloride, filtered and subjected to NMR analysis and trimethylsilyl 7-trimethylsilylamino-3-acetoxymethyl-3-cephem-4-carboxylate appeared to be present for at least 80%.

EXAMPLE 71

Trimethylsilyl 7-trimethylsilylamino-3-(5-methyl-1,3,4-thiadiazolyl-2)-thiomethyl-3-cephem-4-carboxylate A mixture of 0.85 g (2.5 mmoles) of 7-amino-3-(5-methyl-1,3,4-thiadiazolyl-2-)-thiomethyl-3-cephem-4-carboxylic acid, 12 mg (0.07 mmole) of saccharin and 25 ml of chloroform was heated to reflux and 1.6 ml (7.7 mmoles) of hexamethyldisilazane were added thereto. A clear solution was obtained instantaneously and after refluxing for 2 hours, the volatile material was evaporated under reduced pressure and the clear, viscous residue was dissolved in 4 ml of dry carbon tetrachloride and from the NMR spectrum of this solution, it could be concluded that trimethylsilyl 7-trimethylsilylamino-3-(5-methyl-1,3,4-thiadiazolyl-2)-thiomethyl-3-cephem-4-carboxylate was formed for at least 80%.

EXAMPLE 72

Trimethylsilyl 7-trimethylsilylamino-3-(1-trimethylsilyl-1H-1,2,3-triazolyl-5)-thiomethyl-3-cephem-4-carboxylate 1.65 ml (80 mmoles) of hexamethyldisilazane and 1.0 mg (0.002 mmole) of di-4-nitrophenyl N-(4-toluenesulfonyl)phosphoramidate were added to 20 ml of chloroform and the mixture was then refluxed till no more ammonia was evolved which was established by leading the ammonia into water by a stream of dry nitrogen which was passed over the reaction mixture and titration with 1 N sulfuric acid. In 1.5 hours, 2.6 mmoles of ammonia were evolved and then, 0.632 g (2 mmoles) of 7-amino -3-(1H-1,2,3-triazolyl-5)-thiomethyl-3-cephem-4-carboxylic acid was added to the mixture. Reflux was continued under the same conditions till no more ammonia came free and in 1.75 hours, 3 mmoles of ammonia were collected. After evaporating to dryness under reduced pressure, 5 ml of carbon tetrachloride were added to the residue and then the solution was evaporated to dryness to obtain 1.13 g of trimethylsilyl 7-trimethylsilylamino-3-(1-trimethylsilyl-1H-1,2,3-triazolyl-5)-thiomethyl-3-cephem-4-carboxylate which was dissolved in dry carbon tetrachloride.

$^1$H NMR: 0.11 (s, 9H); 0.28 (s, 9H); 0.52 (s, 9H); 1.41 (d, 1H, J 12 Hz); 3.40 and 3.80 (Abq, 2H, J 18 Hz); 3.75 and 4.29 (ABq, 2H, J 13.5 Hz); 4.49 and 4.75, 4.73 (dd and s, 2H J 4.8 Hz); 7.57 (s, 1H).

IR (CCl$_4$): 3400, 1795, 1720, 1380, 1270, 865 cm$^{-1}$.

EXAMPLE 73

Trimethylsilyl 7-trimethylsilylamino-3-(1-methyl-1H-tetrazolyl-5)-thiomethyl-3-cephem-4-carboxylate Using the procedure of Example 72, 1.64 g (4.6 mmoles) of 7-amino-3-(1-methyl-1H-tetrazolyl-5)-thiomethyl-3-cephem-4-carboxylic acid (with a content of 91%) in 30 ml of chloroform were silylated in 2 hours with 3.0 ml (14.4 mmoles) of hexamethyldisilazane using 5.0 mg (0.01 mmole) of di-4-nitrophenyl N-trichloroacetylphosphoramidate as the catalyst. The mixture was concentrated by evaporation in a rotating film evaporator to a foam which was then dried under vacuum to obtain 2.21 g (103%) of trimethylsilyl 7-trimethylsilylamino -3-(1-methyl-1H-tetrazolyl-5)-thiomethyl-3-cephem-4-carboxylate.

$^1$H NMR (CCl$_4$): 0.11 (s, 9H); 0.34 (s, 9H); 1.43 (d, 1H, J 12 Hz); 3.66 (s, 2H); 3.90 (s, 3H); 4.14 and 4.51 (ABq., 2H, J 13.5 Hz); 4.58, 4.83 and 4.82 (dd and s, 2H, J 4.5 Hz).

EXAMPLE 74

Trimethylsilyl 7-D-(o-trimethylsilyl)-mandelamido-3-(1-methyl-1H-tetrazolyl-5)-thiomethyl-3-cephem-4-carboxylate A suspension of 3.23 g (6.3 mmoles) of 7-D-(—) mandelamido-3-(1-methyl-1H-tetrazolyl-5)-thiomethyl-3-cephem-4-carboxylic acid (90%; cefamandole), 10.0 mg (0.02 mmole) of di-4-nitrophenyl N-(4-toluenesulfonyl)-phosphoramidate, 1.90 ml (9.1 mmoles) of hexamethyldisilazane and 30 ml of dichloromethane was refluxed and the ammonia evolved was led into water by a dry stream of nitrogen which was passed over the reaction mixture. It was established by titration with 1 N sulfuric acid that the evolution of ammonia was completed after refluxing for ½ hour and 65 ml of 1 N sulfuric acid had been used. The solid remaining after evaporation to dryness under reduced pressure was washed with a mixture of 20 ml of petroleum ether and 5 ml of ethyl acetate yielding 3.1 g (81%) of trimethylsilyl 7-D-(o-trimethylsilyl)-mandelamido-3-(1-methyl-1H-tetrazolyl-5)-thiomethyl-3-cephem-4-carboxylate. The $^1H$ NMR spectrum was in conformity with that known from literature.

EXAMPLE 75

Trimethylsilyl 7-phenylacetamido-3-(1-methyl-1H-tetrazolyl-5-thio)-methyl-3-cephem-4-carboxylate A solution of 1 ml of dichloromethane containing 0.048 mg (0.00026 mmole) of saccharin was put into a round bottom flask of 25 ml and then the solvent was evaporated under reduced pressure. 113 mg (0.25 mmole) of 7-phenylacetamido-3-(1-methyl-1H-tetrazolyl-5-thio)-methyl-3-cephem-4-carboxylic acid were weighed out in the vessel and then 2 ml of deuterochloroform and 0.05 ml (0.25 mmole) of hexamethyldisilazane were added. While a gentle stream of dry nitrogen was passed through the mixture, it was stirred at room temperature. After 10 minutes, an almost clear solution was obtained and after stirring for 1 hour, a NMR spectrum of the clear solution was recorded, from which it appeared that the silylation had proceeded quantatively to obtain trimethylsilyl 7-phenylacetamido-3-(1-methyl-1H-tetrazolyl-5-thio)-methyl-3-cephem-4-carboxylate.

$^1$H NMR (CDCl$_3$): 0.31 (s, 9H); 3.58 (s, 2H); 3.64 (s, 2H); 3.86 (s, 3H); 4.33 (s, 2H); 4.88 (d, 1H, J 4.5 Hz); 5.78 (dd, 1H, J 4.5 and 9 Hz); 6.22 (d, 1H, J 9 Hz); 7.27 (s, 5H).

EXAMPLE 76

Trimethylsilyl 7-phenylacetamido-3-(1-trimethylsilyl-1H-1,2,3-triazolyl-5-thio)-methyl-3-cephem-4-carboxylate In a round bottom flask of 25 ml, 2 ml of a solution of 0.25 mg (0.0005 mmole) of di-4-nitrophenyl N-trichloroacetylphosphoramidate were evaporated to dryness under reduced pressure and then 103 mg (0.25 mmole) of 7-phenylacetamido-3-(1H-1,2,3-triazolyl-5-thio)-methyl-3-cephem-4-carboxylic acid were weighed out in the vessel and 2 ml of deuterochloroform were added. Then, at reflux 0.10 ml (0.48 mmole) of hexamethyldisilazane was added and reflux was continued for 45 minutes. Then, the mixture was evaporated to dryness under reduced pressure yielding 144 mg of trimethylsilyl 7-phenylacetamido-3-(1-trimethylsilyl-1H-1,2,3-triazolyl-5-thio)-methyl-3-cephem-4-carboxylate.

$^1$H NMR (CDCl$_3$): 0.28 (s, 9H); 0.53 (s, 9H); 3.23, 3.53, 3.64, 3.95 (ABq, 2H, J 18 Hz); 3.61 (s, 2H); 3.68, 3.90, 4.15, 4.39 (ABq, 2H, J 13 Hz); 4.88 (d, 1H, J 4.5 Hz); 5.78 (dd, 1H, J 4.5 and 9 Hz); 6.53 (d, 1H, J 9 Hz); 7.33 (s, 5H); 7.66 (s, 1H).

EXAMPLE 77

Trimethylsilyl 3-methyl-7-phenylacetamido-3-cephem-4-carboxylate 1-oxide 142 mg (0.41 mmole) of 3-methyl-7-phenylacetamido-3-cephem-4-carboxylic acid 1-oxide and 0.5 mg (0.003 mmole) of saccharin were suspended in 3 ml of deuterochloroform and 57 mg (0.297 mmole) of 9-methylanthracene were added as an internal reference for quantitative NMR analysis. 0.05 ml (0.24 mmole) of hexamethyldisilazane was added and the mixture was refluxed for 10 minutes. The clear, pale yellow solution obtained was cooled to room temperature and from the NMR spectrum of this solution, it was calculated, by comparing the integration ratios of the trimethylsilyl ester peak of the trimethylsilyl 3-methyl-7-phenylacetamido-3-cephem-4-carboxylate 1-oxide formed and the methyl peak of the 9-methylanthracene added that the yield of trimethylsilyl 3-methyl-7-phenylacetamido-3-cephem-4-carboxylate 1-oxide was 97%.

EXAMPLE 78

Trimethylsilyl b 7-trimethylsilylamino-3-methyl-3-cephem-4-carboxylate-1$\beta$-oxide and 1$\alpha$-oxide A. 0.2 ml (0.96 mmole) of hexamethyldisilazane were added with stirring to a suspension of 122 mg (0.53 mmole) of 7-amino-3-methyl-3-cephem-4-carboxylic acid-1$\beta$-oxide, 0.5 mg (0.001 mmole) of di-4-nitrophenyl N-(4-toluenesulfonyl)-phosphoramidate and 2 ml of dichloromethane. After refluxing for 6 minutes while passing a dry stream of nitrogen over the reaction mixture, a clear solution was obtained and after refluxing for 40 minutes, the mixture was evaporated to dryness in a rotating film evaporator. The solid residue was dried under vacuum at room temperature to obtain 208 mg of trimethylsilyl 7-trimethylsilylamino-3-methyl-3-cephem-4-carboxylate 1β-oxide.

$^1$H NMR (CDCl$_3$): 0.14 (s, 9H); 0.36 (s, 9H); 1.99 (d, 1H, J 14 Hz); 2.16 (s, 3H); 3.19, 3.60 (ABq, 2H, J 18 Hz); 4.34 (d, 1H, J 4.5 Hz); 4.62, 4.86 (dd, 1H, J 4.5 and 14 Hz).

B. In the same manner, trimethylsilyl 7-trimethylsilylamino-3-methyl-3-cephem-4-carboxylate-1α-oxide was obtained.

$^1$H NMR (CDCl$_3$): 0.17 (s, 9H); 0.34 (s, 9H); 1.54 (d, 1H, J 13 Hz); 2.13 (s, 3H); 3.37 and 3.97 (ABq, 2H, J 17 Hz); 4.44 (d, 1H, H 4.5 Hz); 4.80 and 5.02 (dd, 1H, J 4.5 and 13 Hz).

EXAMPLE 79

1-trimethylsilyl-2-phenylhydrazine 90 mg (0.5 mmole) of saccharin were added to 10.8 g (0.1 mole) of phenylhydrazine and the mixture was heated to 130° C. 15.6 ml (0.075 mole) of hexamethyldisilazane were added and refluxing was continued for 2.5 hours. By the method described in Example 1A, it was established that after refluxing for two hours the calculated amount of ammonia was evolved. Vacuum distillation of the mixture yielded 16.15 g (89.7%) of 1-trimethylsilyl-2-phenylhydrazine boiling at 112°–116° C. at 11 mm Hg and n$_D$ 25 = 1.5241.

EXAMPLE 80

N-trimethylsilyloxysuccinimide

A mixture of 5.60 g (47.2 mmoles) of N-hydroxysuccinimide (purity 97%) and 46 mg (0.25 mmole) of saccharine was heated to 130° C. and 7.8 ml (37.5 mmoles) of hexamethyldisilazane were added. A fierce evolution of ammonia started immediately and was completed 15 minutes after the beginning of the addition of hexamethyldisilazane. The mixture was cooled and excess hexamethyldisilazane was distilled off at reduced pressure. The residue was fractionated to yield 7.70 g (87.2%) of N-trimethylsilyloxysuccinimide boiling at 109°–110° C. at 0.4 mm Hg. and melting at 55°–57° C.

EXAMPLE 81

N-benzoyl-N,O-bis-(trimethylsilyl)-hydroxylamine 4.2 ml (20.2 mmoles) of hexamethyldisilazane were added dropwise quickly to a refluxing mixture of 1.21 g (8.8 mmoles) of benzohydroxamic acid, 5 mg (0.01 mmole) of di-4-nitrophenyl N-(4-toluenesulfonyl)-phosphoramidate and 10 ml of dichloromethane, whereby a precipitate was formed. After refluxing for 15 minutes, the evolution of ammonia had ceased to obtain a clear solution. The volatile materials were removed by evaporation under reduced pressure to obtain 2.35 g (95%) of N-benzoyl-N,O-bis-(trimethylsilyl)-hydroxylamine.

$^1$H NMR (CDCl$_4$): 0.26 (s, 9H); 0.30 (s, 9H); 7.2–7.4 (m, 3H); 7.6 α 7.8 (m, 2H).

EXAMPLE 82

N-trimethylsilyloxy-4-toluenesulfonamide 1.0 ml (4.8 mmoles) of hexamethyldisilazane was added to a refluxing mixture consisting of 0.94 g (5.0 mmoles) of N-hydroxy-4-toluenesulfonamide, 5 mg (0.01 mmole) of tetraphenylimidodiphosphate and 20 ml of dichloromethane and by titration of the ammonia evolved with 0.1 N sulfuric acid, it was established that the evolution of ammonia ceased after refluxing for 50 minutes. At that time, 2.5 mmoles of ammonia had been collected and the reaction mixture was evaporated to dryness to obtain 1.29 g (100%) of N-trimethylsilyloxy-4-toluenesulfonamide melting at 87°–90° C.

$^1$H NMR (CDCl$_4$): 0.17 (s, 9H); 2.43 (s, 3H); 6.90 (s, 1H); 7.20, 7.34, 7.69, 7.83 (q, 4H).

EXAMPLE 83

1-trimethylsilyloxycyclohexen-3-one 8.4 g (72 mmoles) of cyclohexanedione-1,3 (purity 96%) and 70 mg (0.38 mmole) of saccharin were mixed with 60 ml (288 mmoles) of hexamethyldisilazane and the mixture was placed in a preheated oil bath and refluxed. By titrating the ammonia liberated during the reaction, it was found that the calculated amount was expelled in 50 minutes. Refluxing was then continued for 10 minutes and excess hexamethyldisilazane was evaporated in vacuo. The residue was vacuum distilled to obtain 10.67 g (80.5%) of 1-trimethylsilyloxycyclohexen-3-one boiling at 119°–121° C. at 2.0 mm Hg.

EXAMPLE 84

Ethyl 3-trimethylsilyloxy-2-butenoate

A mixture of 9.75 g (75 mmoles) of ethyl acetoacetate and 70 mg (0.38 mmole) of saccharin was heated to 130° C. in a oil bath and 60 ml (288 mmoles) of hexamethyldisilazane were added. The mixture was refluxed for 1.5 hours and excess of hexamethyldisilazane was distilled off at reduced pressure. The residue was vacuum distilled to obtain 12.71 g (84%) of ethyl 3-trimethylsilyloxy-2-butenoate boiling at 102°–104° C. at 16 mm H.

EXAMPLE 85

1-trimethylsilyloxybutane

To a solution of one of the catalysts mentioned in the table below in 15 ml of dichloromethane, a solution of 1.48 g (20.0 mmoles) of butanol-1 in 10 ml of dichloromethane was added and this mixture was heated to reflux 2.50 ml (12.0 mmoles) of hexamethyldisilazane were added and the time (t) in which half of the calculated amount of ammonia was evolved was measured. Further details are to be found in the following table.

| Catalyst | mol-% of catalyst | t in minutes |
|---|---|---|
| none | | 42 |
| di-4-nitrophenyl N—(dimethylaminosulfonyl)-phosphoramidate | 0.5 | 2 |
| diisopropyl N—(dichloroacetyl)-phosphoramidate | 0.5 | 22 |
| di-o-chlorophenyl N—(4-chlorophenylsulfonyl)-phosphoramidate | 1.0 | 17 |
| N,N—dimethylsulfamide | 5.0 | 15 |
| silylated saccharin | 0.1 | 4 |
| N—(1-naphthoyl)-4-toluenesulphonamide | 1.0 | 8 |
| N—(2-methoxybenzoyl)-4-toluenesulphonamide | 5.0 | 22 |

EXAMPLE 86

N,N-dimethyl-N'-trimethylsilylsulfamide 3 ml (14.4 mmoles) of hexamethyldisilazane were added to a refluxing mixture of 2.48 g (20 mmoles) of N,N-dimethylsulfamide, 9 mg (0.05 mmole) of saccharin and 30 ml of toluene. By the method described hereinbefore, it was established that the calculated amount of ammonia had been evolved after refluxing for one hour and volatile materials were then evaporated under reduced pressure. The residue was dried to room temperature to obtain 3.96 g (101%) of N,N-dimethyl-N'-trimethylsilylsulfamide melting at 83°-86° C.

EXAMPLE 87

Trimethylsilyl trimethylsilylthioacetate 4.0 ml (19.2 mmoles) of hexamethyldisilazane were added to a refluxing solution of 1.20 g (13.0 mmoles) of mercaptoacetic acid and 18 mg (0.036 mmole) of di-4-nitrophenyl N-(4-toluenesulfonyl)-phosphoramidate in 10 ml of toluene. By the method described hereinbefore, it was established that the calculated amount of ammonia (13 mmoles) had been evolved after refluxing for 25 minutes and volatile materials were then evaporated in the rotating film evaporator. The residue was kept under vacuum for 0.5 hour to obtain 2.87 g (93.4%) of trimethylsilyl trimethylsilylthioacetate.

$^1$H NMR (CCl$_4$): 0.28 (s, 9H); 0.32 (s, 9H); 3.01 (s, 2H).

Various modifications of the process and products of the invention may be made without departing from the spirit or scope thereof and it is to be understood that the invention is intended to be limited only as defined in the appended claims.

What we claim is:

1. An improved process for the trimethylsilylation of organic compounds with at least one active hydrogen atom with hexamethyldisilazane, the improvement comprising effecting the reaction in the presence of 0.001 to 10 mole percent of a catalyst of the formula

X—NH—Y    I wherein X and Y are individually an electron-withdrawing group or when X is an electron-withdrawing group, Y is selected from the group consisting of hydrogen and trialkylsilyl of 1 to 6 carbon atoms or X and Y together with the nitrogen atom to which they are attached form a cyclic electron-withdrawing group the electron-withdrawing group being selected from the group consisting of

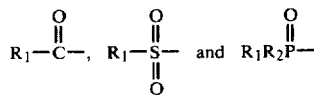

wherein R$_1$ and R$_2$ are individually selected from the group consisting of alkyl of 1 to 6 carbon atoms optionally substituted with at least one halogen, aryl optionally substituted with at least one member of the group consisting of halogen, alkyl and alkoxy of 1 to 6 carbon atoms and nitro, alkoxy of 1 to 6 carbon atoms, aryloxy optionally substituted with at least one member of the group consisting of halogen, alkyl, nitro and

R$_3$ and R$_4$ are individually selected from the group consisting of hydrogen, alkyl of 1 to 6 carbon atoms and trialkylsilyl of 1 to 6 carbon atoms and the electron-withdrawing group which forms a cyclic system together with the nitrogen atom to which they are attached have the formula —A—Z—B wherein A is

B is selected from the group consisting of

and Z is selected from the group consisting of alkylene of 1 to 6 carbon atoms, alkenylene of 2 to 6 carbon atoms and arylene, all optionally substituted with at least one member of the group consisting of halogen and alkyl.

2. The process of claim 1 wherein the electron-withdrawing group is selected from the group consisting of:

 (a)

wherein R$_5$ is selected from the group consisting of alkyl of 1 to 6 carbon atoms optionally substituted by at least one halogen and aryl optionally substituted at least one alkoxy of 1 to 6 carbon atoms or nitro,

 (b)

wherein R$_6$ is selected from the group consistin of methyl and aryl optionally substituted by at least one halogen or methyl, or R$_6$ is R$_7$R$_8$N— wherein R$_7$ and R$_8$ are individually selected from the group consisting of hydrogen, trialkylsilyl and alkyl of 1 to 6 carbon atoms,

 (c)

wherein R$_9$ and R$_{10}$ are individually selected from the group consisting of alkoxy of 1 to 6 carbon atoms and aryloxy optionally substituted by halogen or nitro, and the electron-withdrawing group which forms cyclic system together with the nitrogen atom,

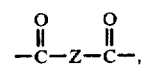 (a')

wherein Z is selected from the group consisting of alkenylene of 2 to 6 carbon atoms optionally substituted by at least one halogen or alkyl and an arylene group optionally substituted by at least halogen and

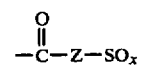 (b')

wherein X is 0, or 2 and Z is alkylene or arylene.

3. The process of claim 1 wherein the electron-withdrawing group is selected from the group consisting of

  (A)

wherein $R_5$ is selected from the group consisting of dihalomethyl, trihalomethyl and phenyl or naphthyl, each optionally substituted by a methoxy group,

  (B)

wherein $R_6$ is selected from the group consisting of methyl, phenyl optionally substituted by methyl or chlorine atom, amino, dialkylamino and trialkylsilylamino and

  (C)

wherein $R_9$ and $R_{10}$ are individually selected from the group consisting of methoxy, ethoxy or propoxy group and phenyl optionally substituted by nitro, chlorine and the electron-withdrawing group which forms a cyclic system together with the nitrogen atom,

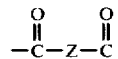  (A')

wherein Z is selected from the group consisting of ethenylene, phenylene and naphthylene each optionally perhalo substituted and

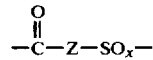  (B')

wherein x is 0 or 2, and Z is phenylene.

4. The process of claim 1 wherein the catalyst is selected from the group consisting of trichloroacetamide, pthalimide, 3,4,5,6-tetrachlorophthalimide, 3,4,5,6-tetrabromophthalimide, 1,8-naphthalimide, maleimide, barbituric acid, saccharin, N-benzyl-4-toluenesulfonamide, N-(2-methoxybenzoyl)-4-toluenesulfonamide, N-(1-naphthoyl)-4-toluenesulfonamide, N-benzoylbenzenesulfonamide, N-(2-methoxy-1-naphthoyl)-4-toluenesulfonamide, N-(2-methoxy-1-naphthoyl)-methane sulfonamide, di-(4-toluenesulfonyl)-amine, dimethyl N-(trichloroacetyl)-phosphoramidate, di-4-nitrophenyl N-(trichloroacetyl)-phosphoramidate, di-4-nitrophenyl N-(p-toluenesulfonyl)-phosphoramidate, diisopropyl N-(dichloroacetyl)-phosphoramidate, di-o-chlorophenyl N-(4-chlorophenylsulfonyl)-phosphoramidate, tetraphenyl imidodiphosphate, sulfamide, N,N-dimethylsulfamide, N,N'-bis-(trimethylsilyl)-sulfamide, 1,2-benzisothiazol-3(2)-one and 4-benzoyloxy-1,2-dihydro-1-oxo-phthalazine.

5. The process of claim 4 wherein the catalyst is selected from the group consisting of saccharin, di-4-nitrophenyl N-(trichloroacetyl)-phosphoramidate, di-4-nitrophenyl N-(4-toluenesulfonyl)-phosphoramidate and tetraphenyl imidodiphosphate.

6. The process of claim 1 for the preparation of compounds of the formula

wherein R is a five- or six-membered heterocyclic having one or more nitrogen or sulfur atoms as the hetero atoms, which group is optionally substituted by at least one member of the group consisting of alkyl of 1 to 6 carbon atoms, phenyl, trimethylsilyl, alkylamino and trimethylsilyloxycarbonylmethyl.

7. The process of claim 6 wherein R is selected from the group consisting of 1,3,4-thiadiazolyl, 1,2,3,4-tetrazolyl, 1,2,3-triazolyl, 1,2,4-triazolyl, an imidazolyl and a pyrimidyl, which are optionally substituted by a member of the group consisting of methyl, phenyl, methylamino, trimethylsilyl and trimethylsilyloxycarbonylmethyl.

8. The process of claim 6 wherein the compound is selected from the group consisting of (5-methyl-1,3,4-thiadiazole-2-thio)-trimethylsilane, 1-methyl-5-trimethylsilylthiotetrazole, 1-trimethylsilyl-5-trimethylsilylthio-1,2,3-triazole, 1-methyl-2-(trimethylsilylthio)-imidazole, 1-trimethylsilyl-3-trimethylsilylthio-1H-1,2,4-triazole, 1-phenyl-5-trimethylsilylthio-1H-tetrazole, 4,6-dimethyl-2-(trimethylsilylthio)-pyrimidine, 2-methylamino-5-trimethylsilylthio-1,3,4-thiadiazole, trimethylsilyl 5-trimethylsilylthio-1H-tetrazolyl-1-acetate, trimethylsilyl 5-trimethyl-silylthio-1,3,4-thiadiazolyl-2-acetate.

9. The process of claim 1 wherein the catalyst is added to the reaction mixture in a masked form.

10. The process of claim 9 wherein the masked form is a silylated derivative, a sodium salt or any other derivative which decomposes in the reaction mixture to the catalytic compounds of claim 1.

* * * * *